United States Patent
Cao

(10) Patent No.: US 11,680,094 B2
(45) Date of Patent: Jun. 20, 2023

(54) METHODS FOR THE PREVENTION AND TREATMENT OF ENTHESOPATHY AND RELATED DISORDERS

(71) Applicant: THE JOHNS HOPKINS UNIVERSITY, Baltimore, MD (US)

(72) Inventor: Xu Cao, Ellicott City, MD (US)

(73) Assignee: THE JOHNS HOPKINS UNIVERSIY, Baltimore, MD (US)

( * ) Notice: Subject to any disclaimer, the term of this patent is extended or adjusted under 35 U.S.C. 154(b) by 177 days.

(21) Appl. No.: 16/763,597

(22) PCT Filed: Nov. 13, 2018

(86) PCT No.: PCT/US2018/060586
§ 371 (c)(1),
(2) Date: May 13, 2020

(87) PCT Pub. No.: WO2019/099334
PCT Pub. Date: May 23, 2019

(65) Prior Publication Data
US 2020/0283513 A1    Sep. 10, 2020

Related U.S. Application Data

(60) Provisional application No. 62/585,065, filed on Nov. 13, 2017.

(51) Int. Cl.
| | |
|---|---|
| A61K 39/395 | (2006.01) |
| C07K 16/22 | (2006.01) |
| A61K 31/4178 | (2006.01) |
| A61K 39/00 | (2006.01) |

(52) U.S. Cl.
CPC .......... C07K 16/22 (2013.01); A61K 31/4178 (2013.01); *A61K 2039/505* (2013.01); *C07K 2317/20* (2013.01); *C07K 2317/76* (2013.01)

(58) Field of Classification Search
None
See application file for complete search history.

(56) References Cited

FOREIGN PATENT DOCUMENTS

| RU | 2555776 C1 | 10/2015 | | |
|---|---|---|---|---|
| WO | 2003/066081 A2 | 8/2003 | | |
| WO | WO-2016130897 A1 * | 8/2016 | ........... | A61K 31/517 |

OTHER PUBLICATIONS

Apostolakos et al. (Muscles, Ligaments and Tendons Journal 4(3): 333-342, 2014).*
Bionity.com, (https://www.bionity.com/en/encyclopedia/Enthesopathy.html) accessed on Jul. 11, 2022.*
McGonagle et al. The Lancet 352: 1137-1140, 1998.*
Vander Ark et al. Cellular Signalling 52: 112-120, 2018.*
Zhen et al. Nat. Med. 19(6): 704-712, 2013.*
Killian, M., et al., "Scleraxis is required for the development of a functional tendon enthesis" The FASEB Journal, vol. 30, Jan. 2016.
Kovacevic, D., et al., "Calcium-Phosphate Matrix With or Without TGF-b3 Improves Tendon-Bone Healing After Rotator Cuff Repair" The American Journal of Sports Medicine, vol. 39, No. 4, (2011) DOI: 10.1177/0363546511399378.

* cited by examiner

*Primary Examiner* — Christine J Saoud
(74) *Attorney, Agent, or Firm* — Casimir Jones, SC; Robert A. Goetz

(57) ABSTRACT

The present invention shows that TGF-β is activated in tendon-bone insertion in both a semi-Achilles tendon transection (SMTS) mouse model and a dorsiflexion immobilization (DI) mouse model of enthesopathy. High concentrations of active TGF-β recruited mesenchymal stromal/stem cells (MSCs) and led to excessive vessel formation, bone deterioration and fibrocartilage calcification. The invention provides uses and methods for prophylaxis and treatment of enthesopathies by inhibition of TGF-β.

13 Claims, 16 Drawing Sheets

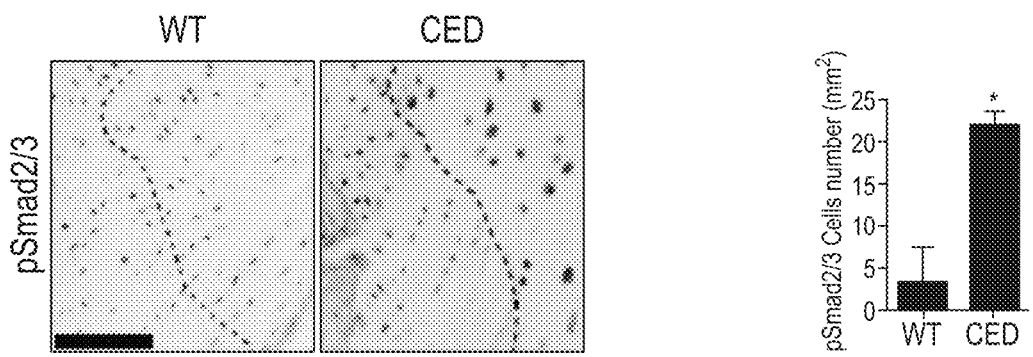
FIG. 3A
FIG. 3B
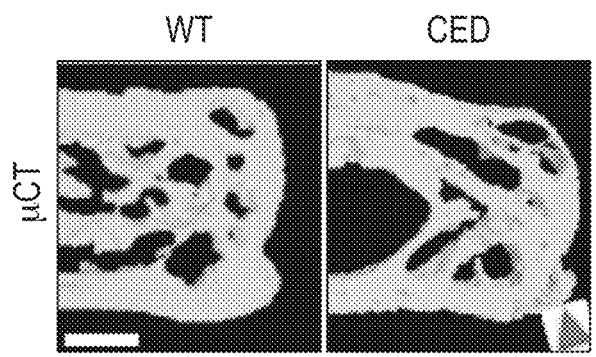
FIG. 3C
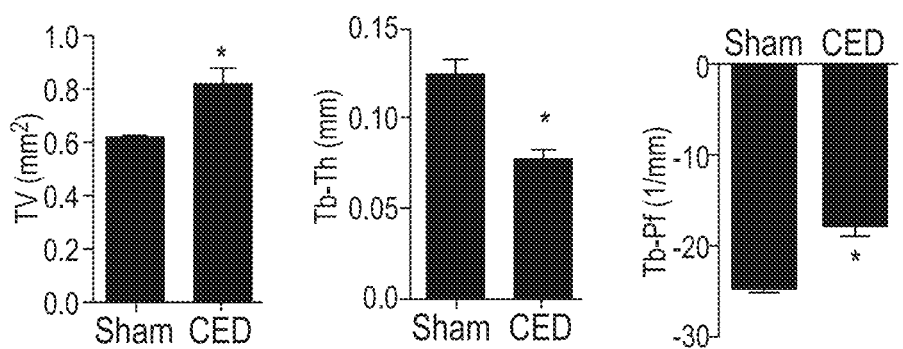
FIG. 3D

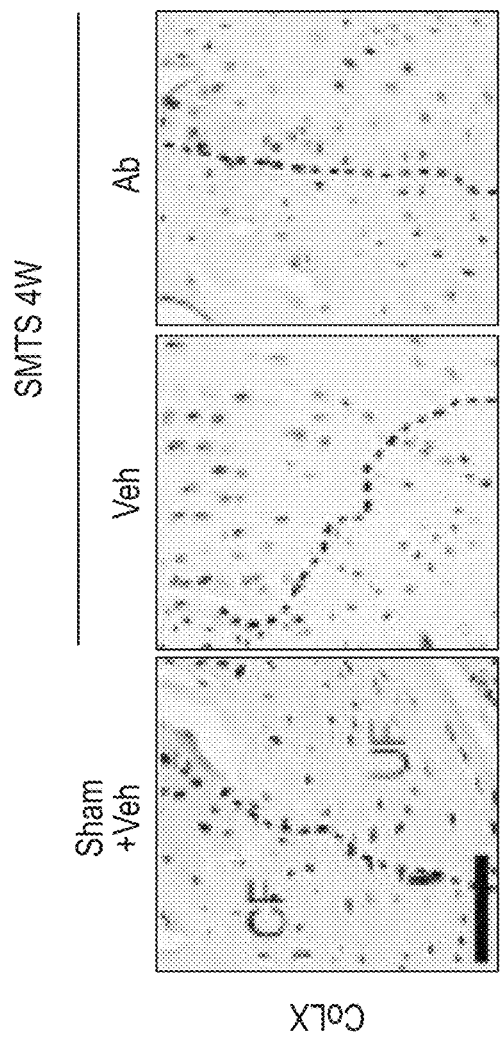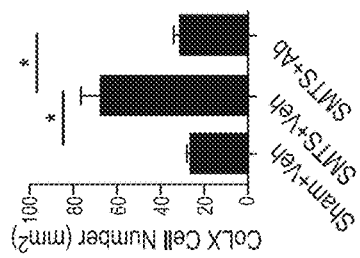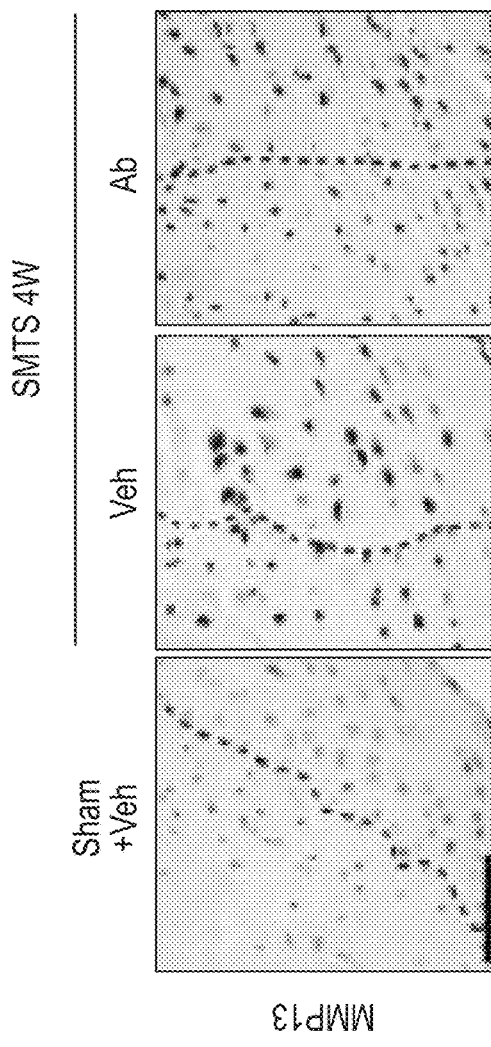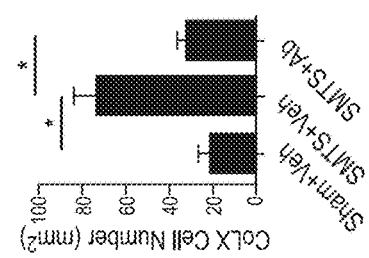

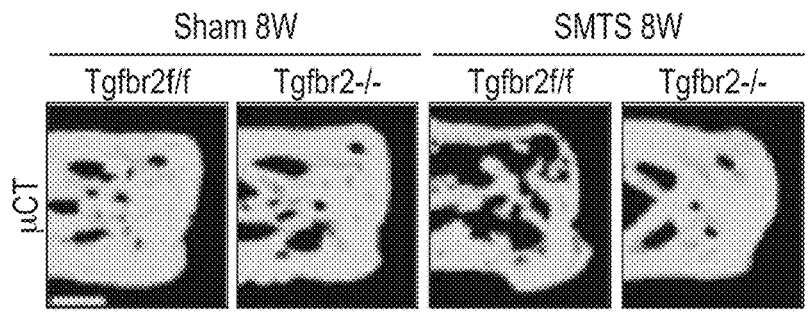
FIG. 6A
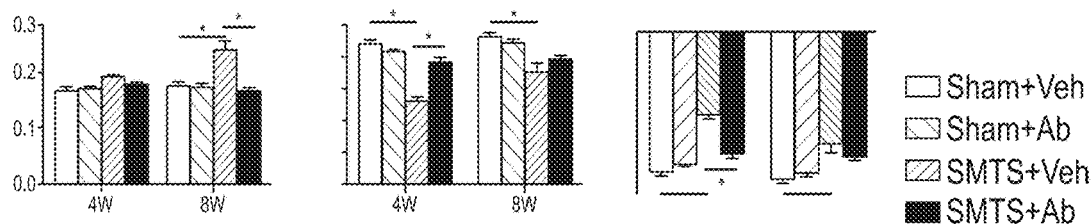
FIG. 6B
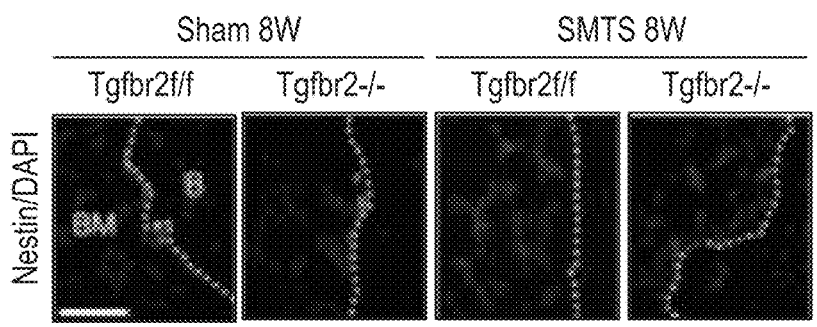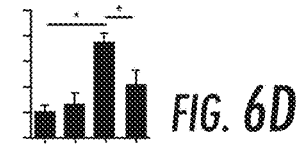
FIG. 6C
FIG. 6D
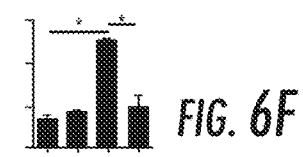
FIG. 6E
FIG. 6F
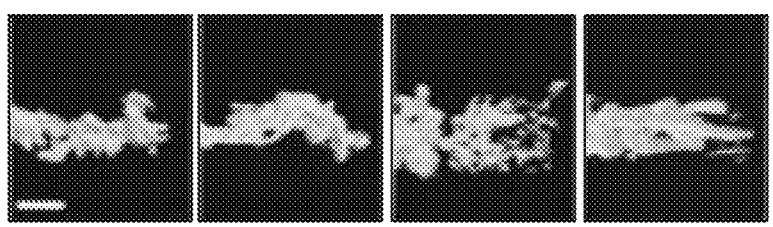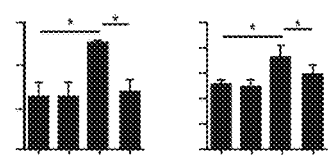
FIG. 6G
FIG. 6H

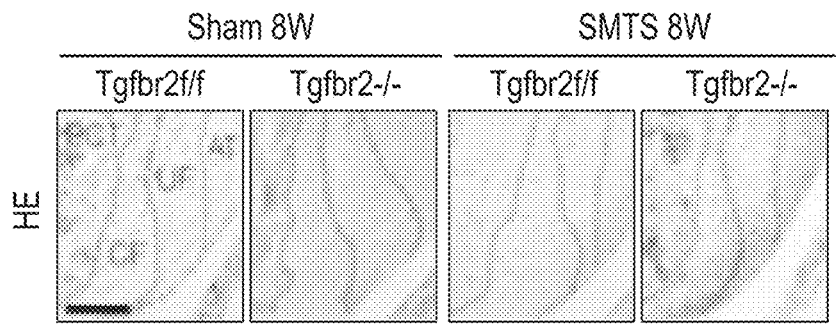
FIG. 6I
FIG. 6J
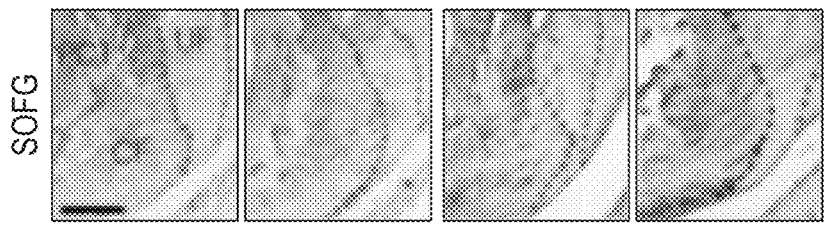
FIG. 6K
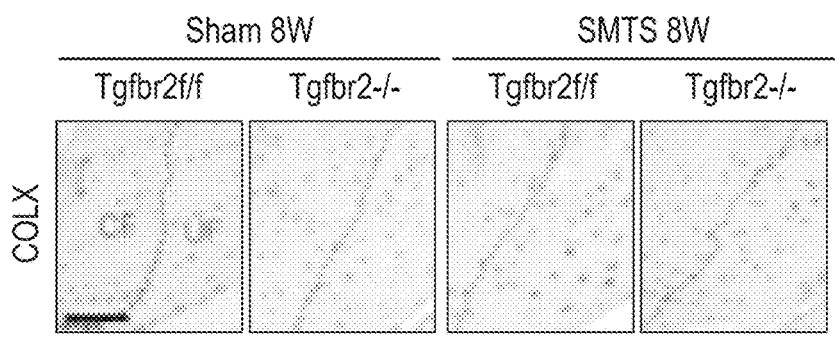
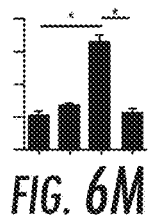
FIG. 6M
FIG. 6L
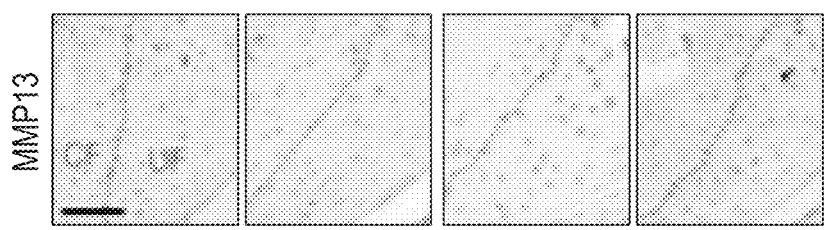
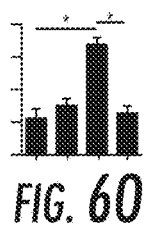
FIG. 6O
FIG. 6N

METHODS FOR THE PREVENTION AND TREATMENT OF ENTHESOPATHY AND RELATED DISORDERS

CROSS-REFERENCE TO RELATED APPLICATIONS

This application is a 35 U.S.C. § 371 U.S. national entry of International Application PCT/US2018/060586, having an international filing date of Nov. 13, 2018, which claims the benefit of U.S. Provisional Application No. 62/585,065, filed Nov. 13, 2017, the content of each of the aforementioned applications is herein incorporated by reference in their entirety.

STATEMENT OF GOVERNMENTAL INTEREST

This invention was made with government support under grant no. AR063943, awarded by the National Institutes of Health. The government has certain rights in the invention.

BACKGROUND OF THE INVENTION

The connection of muscles to bones via tendons or ligaments is vital for movement. The entheses, the insertion sites of tendons or ligaments to bones, are essential for a smooth mechanical transfer of load between muscles and bones.[1] Disorders involving the attachment of connective tissue to bone are referred to as enthesopathy, resulting in a disturbance of the load transfer[2]. Over half of sports injuries involve tendons and enthuses.[3,4] Tendon disorders, which include enthesopathy, represent a considerable socioeconomic burden, estimated to be S850 billion per year in health care costs and indirect lost wage expenditures according to the American Public Health Association.[5,6] Enthesopathy not only results from injuries including sports, but can be an important feature of a considerable number of other disorders and pathogeneses, such as spondyloarthropathy. There are two types of enthuses,[7] fibrous entheses and fibrocartilaginous entheses. Fibrous entheses, such as medial collateral ligament enthesis in the knee, provide a direct attachment of the tendon or ligament to the bone via the periosteum. Fibrocartilaginous entheses, such as Achilles tendon enthesis and anterior cruciate ligament enthesis, are the more predominant type of entheses in humans, composed of four transitional zones including: tendon/ligament, un-calcified fibrocartilage, calcified fibrocartilage and bone with graded mechanical properties.[8,9]

Enthesopathy can be defined histologically, including fibrocartilage degeneration, micro-fracture and/or bone necrosis, angiogenesis, and disruption of the tidemark which is the calcified-noncalcified cartilage interface.[10-12] In healthy fibrocartilage, type II collagen is the most abundant collagenous extra cellular matrix (ECM) protein along with proteoglycans.[13-17] ECM turnover remains at relatively low rates and resists proliferation and differentiation. During degeneration, type X collagen and MMP13 are over-expressed in fibrocartilage with lower amounts of proteoglycans, decreased un-calcified fibrocartilage zone and expanded calcified fibrocartilage zone.[18-21] Blood vessels and bony defects are also often present and the blood vessels may pass between the tendon/ligament and the bone marrow.[22] Abnormal calcification or ossification of the tendon or ligament, known as enthesophytes, may occur at the late stage and can be observed radiographically. Calcaneal enthesophytes at the insertion of the plantar aponeurosis are seen in 25% of the general population.[23-25]

Despite the well-described histological features of enthesopathy, little is known about the cell signaling mechanisms that contribute to the pathogenesis. The role of TGF-β in musculoskeletal disease has drawn increasing attention in recent years. During tissue injury or remodeling, TGF-β is activated to recruit stem/progenitor cells to maintain tissue homeostasis. It was previously shown that TGF-β is released from the bone matrix and activated during osteoclastic bone resorption.[26] Active TGF-β induces mesenchymal stromal/stem cells (MSCs) migration to the bone resorptive pits for new bone formation.[26] However, excessive active TGF-β leads to uncoupled bone remodeling, contributing to the pathogenesis of rare genetic skeletal diseases such as Camurati-Engelmann disease (CED), osteogenesis imperfecta, and more common musculoskeletal disorders, such as osteoarthritis.[26-31] High levels of TGF-β have been observed locally and systemically in spondyloarthropathy patients with enthesopathy.[32,33]

TGF-β plays an essential role in cartilage and bone homeostasis and relies on precise spatial and temporal activation.[26,52] It is expressed as an inactive latent form and deposited in the ECM in mammals.[41] TGF-β isoforms are broadly expressed in bone, cartilage, and tendon. In the bone remodeling microenvironment activation of bone matrix TGF-β1 leads to migration of MSCs for osteogenesis.[26] In cartilage, TGF-β stimulates the production of extracellular matrix proteins and prevents terminal differentiation of chondrocytes.[53,54] In tendons, TGF-β influences the direction of, the enthesis fibrocartilage, aligning with compressive forces.[55,56] Disruption of the precise temporal and spatial activation of TGF-β contributes to the pathology. The inventors' previous study showed that high concentrations of active TGF-β1 in subchondral bone increased the number of MSCs and osteoprogenitors to disrupt the joint microarchitecture and contributed to the pathogenesis of osteoarthritis.[31] Given the increasing incidence of tendon injuries,[76] identifying and initiating treatment before tendon rupture is paramount.

As such, there exists an unmet need for understanding the biological mechanisms which lead to enthesopathy and therapies to treat them.

SUMMARY OF THE INVENTION

In healthy fibrocartilaginous enthesis, such as the Achilles' tendon, four layers of transitional zone act as a functional unit.[1] The four transitional zones confer a smooth transfer of load by giving rise to graded tissue mechanical properties.[1] Semi-transection of the Achilles' tendon disrupts the force transmission while leaving the enthesis intact.

In accordance with the present invention, the inventors found that uneven mechanical force on the Achilles' tendon entheses increased bone resorption as demonstrated by an increase in the TRAP staining in the PCT bone as early as 7 days after surgery in both the SMTS and DI mouse model. The increased osteoclastic activity was associated with activation of TGF-β, increased Nestin$^+$ cell numbers and subsequent excessive bone formation and angiogenesis. At the same time, degenerative changes were noted in the enthesis, revealed by increased CF area, decreased UF area and high expression of MMP13 and COL X in the fibrocartilage. The role of excessive active bone marrow TGF-β in enthesopathy was further affirmed utilizing the CED mice.

In accordance with one or more embodiments of the present invention, the inventors determined the role of TGF-β in Achilles tendon enthesopathy using three different mouse models. It was found that the changes of calcaneal bone microstructure and composition associated with the onset of Achilles tendon enthesopathy. In addition, it was surprisingly found that inhibition of TGF-β activity, using either a TGF-β neutralizing antibody (1D11) or a conditional knockout mouse model, attenuated calcaneal and fibrocartilage pathological changes, and treated or prevented enthesopathy in the models studied.

The inventors found that inhibition of TGF-β activity was effective in preventing changes in the PCT microarchitecture and enthesis degeneration. Similar to their findings in osteoarthritis, where microarchitectural changes in subchondral bone led to articular cartilage degeneration, the deletion of tgfb2r in Nestin lineage cells after SMTS preserved the PCT integrity with no statistically significant differences relative to Sham groups. The inventors' data also demonstrated that TGF-β antibody treatment involves not only inhibition of Smad phosphorylation, but also a marked drop in Nestin$^+$ cell number as well as bone and vessel formation. Recent studies demonstrate Nestin$^+$ cells can give rise to endothelial cells and mesenchymal lineage cells.[42-44] The decrease in Nestin$^+$ cell numbers in the TGF-β antibody SMTS mice are consistent with our prior data[26] regarding the role of TGF-β in MSCs migration and likely explain the decrease in vessel and bone formation.

Most importantly, deletion of tgfb2r in Nestin lineage cells attenuated enthesis degeneration, confirming that the bone, enthesis, tendon act as a functional unit. The precise role of TGF-β in the bone-tendon unit, however, appears to be complicated, perhaps with spatially and temporally dependent roles. Specifically, control of TGF-β signaling has been shown to be both beneficial and detrimental, depending on the models utilized. Inhibition of the TGF-β type 1 receptor demonstrated promising results for tendon repair after injuries.[57] However, in a rat rotator cuff tendon-to-bone healing model, in which the enthesis was completely resected and the tendon was then reattached to the bone, inhibition of various TGF-β isoforms did not lead to regenerative healing.[60]

In accordance with the methods of the present invention, the inventors purposely preserved the Achilles' tendon enthesis by partially transecting the Achilles' tendon, leaving the native enthesis intact to specifically study the initial phase of enthesopathy, which may account for our different results.

In accordance with one or more embodiments of the present invention, the inventors provide methods of tissue-oriented therapy that specifically inhibits TGF-β activity which is a novel approach for treating enthesopathy. Indeed, the inventors found that systemic administration of the TGF-β antibody attenuated the initiation and progression of enthesopathy in various mouse models.

It will be understood by those of ordinary skill in the art that in addition to the antibody used in the experimental methods described herein, there are several candidate drugs currently in use clinically or in clinical trials to consider for future preclinical or clinical trials of enthesopathy.[66] For example, losartan, an angiotensin receptor blocker that is known to suppress the TGF-β signaling cascade.

There are also multiple drugs that more specifically target the TGF-β signaling pathway being explored in clinical trials, such as Fresolimumab and Galunisertib.[69-73] The most recent results utilizing a TGF-β monoclonal antibody were in Phase 2 trial in systemic sclerosis and suggest the TGF-β antibody has a reasonable safety profile.[72] However, there are also concerns regarding blockade of TGF-β signaling. For example, chronic, non-healing wounds often show a loss of TGF-β1 signaling.[74,75] Therefore, a delay in wound healing could be of potential concern upon TGF-β antagonist treatment.

In accordance with a first embodiment, the present invention provides a method for the prevention and/or treatment of enthesopathy or an associated disorder in subject in need thereof comprising administering to the subject an effective amount of a transforming growth factor-β (TGF-β) inhibitor.

In accordance with a second embodiment, the present invention provides a method for the prevention and/or treatment of enthesophytes in the Posterior Calcaneal Tuberosity (PCT) and/or enthesis degeneration of the Achilles tendon of a subject in need thereof, comprising administering to the subject an effective amount of a transforming growth factor-β (TGF-β) inhibitor.

In accordance with a third embodiment, the present invention provides a method for the prevention or reduction of the population of nestin+ bone marrow precursor cells in the bone marrow of a subject suffering from an enthesopathy or an associated disorder comprising administering to the subject an effective amount of a transforming growth factor-β (TGF-β) inhibitor.

In accordance with a fourth embodiment, the present invention provides a method for the prevention and/or treatment of decreased bone or vessel formation in an enthesis of a subject comprising administering to the subject an effective amount of a transforming growth factor-β (TGF-β) inhibitor.

In accordance with a fifth embodiment, the present invention provides a method for the prevention and/or treatment of bone resorption in an enthesis of a subject comprising administering to the subject an effective amount of a transforming growth factor-β (TGF-β) inhibitor.

In accordance with a sixth embodiment, the present invention provides a method for the prevention or treatment of a stress injury in an enthesis of a subject comprising administering to the subject an effective amount of a transforming growth factor-β (TGF-β) inhibitor.

BRIEF DESCRIPTION OF THE DRAWINGS

FIGS. 3A-3H illustrate that CED mice show an Achilles' tendon enthesopathy phenotype. (3a) Immunohistochemical analysis of pSmad2/3+ cells (brown) in Achilles' tendon enthesis fibrocartilage of 4-month-old CED mice and WT littermates. Scale bar, 100 μm. (3b) Quantitative analysis of the number of pSmad2/3+ cells per tissue area ($mm^2$). (3c) μCT images of the PCT (sagittal view). Red arrowhead suggests enthesophyte-like structure formation. Scale bar, 500 μm. (3d) Quantitative analysis of TV, Tb.Th and Tb.Pf in PCT determined by μCT analysis. (3e) Immunostaining and (3f) quantitative analysis of Nestin+ (red) cells in the PCT bone marrow 4 weeks after sham and SMTS operation. Scale bar, 30 μm. (3g) μCT-based microangiography of the calcaneus and (3h) quantitative analysis of Vessel Number (VN) and Vessel Volume (VV). Scale bar, 100 μm. (3i) Immunostaining and (3j) quantitative analysis of Osx+ (brown) cells in the PCT bone marrow 4 weeks after sham and SMTS operation. Scale bar. 50 μm. (3k) H&E staining of Achilles tendon enthesis. The PCT bone, CF and UF are separated by dotted lines. T, Achilles Tendon. Scale bar, 200 μm. (3l) Quantitative analysis of area of CF and UF. (3m) SOFG staining of Achilles tendon enthesis. Scale bars, 200 μm. Data shown as Mean±SEM. n=10. *P<0.05 compared between groups.

FIGS. 5A-5G depict systemic injection of TGFβ1 antibody attenuates enthesis degeneration, new bone formation and angiogenesis. (5a) H&E staining of Achilles' tendon enthesis. PCT, CF, UF and Achilles' Tendon (T) are separated by dotted lines. Scale bar, 200 μm. (5b) Quantitative analysis of area of CF) and UF. (5c) SOFG staining of Achilles' tendon enthesis. Scale bar, 200 μm. (5d, 5f) Immunohistochemical (staining) and (5e, 5g) quantitative (bar chart, right) analysis of (5d, 5e) COLX+ cells and (5f, 5g) MMP13+ cells (bottom) in fibrocartilage (CF and UF are separated by dotted line), of mouse Achilles' tendon enthesis after SMTS surgery. Scale bars, 150 μm. 4 W, four weeks after SMTS surgery; 8 W, eight weeks after SMTS surgery. Data shown as Mean±SEM. n=10. *P<0.05 compared between groups or to the sham group.

FIGS. 6A-6O show that genetic knockout of Tgfβr2 in Nestin+ cells results in less change in Achilles' tendon enthesis after SMTS. (6a) μCT images of the PCT (sagittal view) of Nestin-creTMEr:Tgfβr2flox/flox (Tgfβr2$^{-/-}$) mice 2 months treated with vehicle or tamoxifen after undergoing sham or SMTS surgery. Scale bar, 500 μm. (6b) Quantitative analysis of structural parameters of PCT by μCT analysis. n=6 per group. (6c) Nestin+ (red) and (6e) Osx+ (brown) cells in the PCT bone marrow treated with vehicle or tamoxifen 8 weeks after sham and SMTS operation. White dotted lines (6c) indicate bone surface. B, Bone; BM, Bone Marrow. Scale bars, 30 μm (6c), 50 μm (6e). (6d, 6f) Quantifications of the number of bone marrow cells positive for Nestin and Osx (per $mm^2$). (6g) μCT-based microangiography of the calcaneus and (6h) quantitative analysis of VN and VV. Scale bar, 100 μm. (i) H&E staining of Achilles' tendon enthesis. PCT, CF, UF and Achilles' Tendon (T) are separated by dotted lines. Scale bar, 200 μm. (6j) Quantitative analysis of area of CF and UF. (6k) SOFG of Achilles' tendon enthesis. Scale bars, 200 μm. (6l, 6m) immunohistochemical and (6m, 6o) quantitative analysis of (6l, 6m) COLX cells and (6n, 6o) MMP13 in enthesis fibrocartilage. Scale bar, 150 μm. 4 W, four weeks after SMTS surgery; 8 W, eight weeks after SMTS surgery. Data shown as Mean±SEM. n=10. *P<0.05 compared between or to the sham group.

Figure 1A:
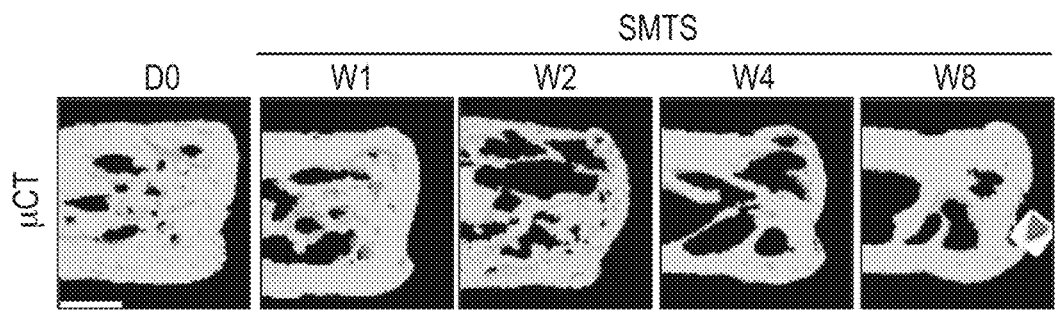
FIGS. 1A-1G depict upregulated TGFβ signaling is associated with enthesopathy in SMTS mice. (1a) Micro CT images of the PCT (sagittal view). Red arrowhead indicates altered morphology of the PCT. Scale bar, 500 μm. (1b) Quantitative analysis of TV, Tb.Th and Tb.Pf in PCT determined by μCT analysis. (1c) TRAP staining (magenta) in mouse PCT bone marrow. Scale bar, 200 μm. (1d) Quantitative analysis of TRAP+ osteoclast surface (Oc.srf) per Bone Surface (Bone Srf). (1e) Quantitative analysis of active TGFβ in peripheral serum by ELISA. (1f) Immunohistochemical analysis of pSmad2/3+ cells (brown) in mouse PCT bone marrow. Scale bar, 100 μm. (1g) Quantitative analysis of the number of pSmad2/3+ cells per bone marrow area (mm$^2$). D0, prior to SMTS surgery. Sham, sham-surgery; W1, one week after SMTS surgery; W2, two weeks after SMTS surgery; W4, four weeks after SMTS surgery; W8, eight weeks after SMTS surgery. Data shown as Mean±SEM. n=10. *P<0.05 compared to the sham group.

or vehicle antibody (13C4) intraperitoneally three times a week (3/W), once a week (1/W) and once a month (1/M) for 30 d. (9b) Quantitative analysis of area of CF and UF at Achilles' enthesis. *P<0.05 compared to the Sham-Vehicle group.

DETAILED DESCRIPTION OF THE INVENTION

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Tendon injuries occur most commonly from excessive or unbalanced strain, such as work-related injuries or sports-related injuries and therefore affect both young and old adults.[2,45] Repair of a tendon after a rupture is difficult and often results in continued pain and disability.[46-48] Histopathologic studies have shown clear degenerative changes before tendon rupture.[49] Potential preventive targets for therapy could be utilized by earlier identification and intervention.

In accordance with one or more embodiments of the present invention, the inventors focused on pathological changes on the enthesis as one fourth of tendon rupture happens in enthesis, and is the most difficult condition to treat.[50,51]

In accordance with a first embodiment, the present invention provides a method for the prevention and/or treatment of enthesopathy or an associated disorder in subject in need thereof comprising administering to the subject an effective amount of a transforming growth factor-β (TGF-β) inhibitor.

In some embodiments the present invention provides the use of subject an effective amount of a transforming growth factor-β (TGF-β) inhibitor for the prevention and/or treatment of enthesopathy or an associated disorder in subject in need thereof.

As used herein, the term "a transforming growth factor-β (TGF-β) inhibitor" means a small molecule, antibody or functional portion or fragment thereof, proteins, peptides, siRNAs, antagonists, agonists, compounds, or nucleotide constructs which either reversibly or irreversibly bind TGF-β and prevent its binding to a TGF-β receptor on a cell or tissue in a subject. The term can also mean a small molecule, antibody or functional portion or fragment thereof, proteins, peptides, siRNAs, antagonists, agonists, compounds, or nucleotide constructs which either reversibly or irreversibly bind TGF-β receptors in an antagonistic manner such that TGF-β and its analogs or derivatives cannot stimulate the TGF-β receptors in cells and tissues in a subject. Examples of TGF-β inhibitors include, for example, antibodies such as (1D11), Fresolimumab, Galunisertib, Lerdelimumab (CAT-152), Metelimumab (CAT-192), GC-1008, SR-2F, and 2G7, small molecule inhibitors such as GW788388 (4-{4-[3-(Pyridin-2-yl)-1H-pyrazol-4-yl]-pyridin-2-yl}-N-(tetrahydro-2H-pyran-4-yl)benzamide hydrate); LY-364947 (4-[3-(2-pyridinyl)-1H-pyrazol-4-yl]-quinoline), RepSox (2-[3-(6-Methyl-2-pyridinyl)-1H-pyrazol-4-yl]-1,5-naphthyridine), SB 431542 (4-(5-Benzol[1,3]dioxol-5-yl-4-pyridin-2-yl-1H-imidazol-2-yl)-benzamide hydrate), LY-550410, LY-580276, LY-2109761, and SX-007, antisense oligonucleotides such as AP-11014, AP-12009, and NovaRx, aptamers such as Trx-xFoxHlb, antisense vaccines such as Trx-Lef1 and Lucanix, soluble antagonists such as TGFβRII:Fc, and Betaglycan/TGFβRIII, and angiotensin II antagonists such as losartan and valsartan and the like.

In accordance with a second embodiment, the present invention provides a method for the prevention and/or treatment of enthesophytes in the Posterior Calcaneal Tuberosity (PCT) and/or enthesis degeneration of the Achilles tendon of a subject in need thereof, comprising administering to the subject an effective amount of a transforming growth factor-β (TGF-β) inhibitor.

In some embodiments, the present invention provides the use of an effective amount of a transforming growth factor-β (TGF-β) inhibitor for the prevention and/or treatment of enthesophytes in the Posterior Calcaneal Tuberosity (PCT) and/or enthesis degeneration of the Achilles tendon of a subject in need thereof.

In accordance with a third embodiment, the present invention provides a method for the prevention or reduction of the population of nestin+ bone marrow precursor cells in the bone marrow of a subject suffering from an enthesopathy or an associated disorder comprising administering to the subject an effective amount of a transforming growth factor-β (TGF-β) inhibitor.

In some embodiments, the present invention provides the use of an effective amount of a transforming growth factor-β (TGF-β) inhibitor for the prevention or reduction of the population of nestin+ bone marrow precursor cells in the bone marrow of a subject suffering from an enthesopathy or an associated disorder.

In accordance with a fourth embodiment, the present invention provides a method for the prevention and/or treatment of decreased bone or vessel formation in an enthesis of a subject comprising administering to the subject an effective amount of a transforming growth factor-β (TGF-β) inhibitor.

In some embodiments, the present invention provides the use of an effective amount of a transforming growth factor-β (TGF-β) inhibitor for the prevention and/or treatment of decreased bone or vessel formation in an enthesis of a subject.

In accordance with a fifth embodiment, the present invention provides a method for the prevention and/or treatment of bone resorption in an enthesis of a subject comprising administering to the subject an effective amount of a transforming growth factor-β (TGF-β) inhibitor.

In some embodiments, the present invention provides the use of an effective amount of a transforming growth factor-β (TGF-β) inhibitor for the prevention and/or treatment of bone resorption in an enthesis of a subject.

In accordance with a sixth embodiment, the present invention provides a method for the prevention or treatment of a stress injury in an enthesis of a subject comprising administering to the subject an effective amount of a transforming growth factor-β (TGF-β) inhibitor.

In some embodiments, the present invention provides the use of an effective amount of a transforming growth factor-β (TGF-β) inhibitor for the prevention or treatment of a stress injury in an enthesis of a subject.

"Treating" or "treatment" is an art-recognized term which includes curing as well as ameliorating at least one symptom of any condition or disease. Treating includes reducing the likelihood of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level.

The dose of the TGF-β inhibitors, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound to be used can be about 0.001 to about 1000 mg/kg body weight of the subject being treated/day, from about 0.01 to about 100 mg/kg body weight/day, about 0.1 mg to about 10 mg/kg body weight/day, including 0.5, 1.0, 2.0, 3.0, 4.0, 5.0, 6.0, 7.0, 8.0, and 9.0 mg/kg body weight/day. In some embodiments, the preferred dosage of the compound is about 5 mg/kg body weight/day.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

As used herein, the terms "stability" and "stable" in the context of a liquid formulation comprising a biopolymer of interest that is resistant to thermal and chemical aggregation, degradation or fragmentation under given manufacture, preparation, transportation and storage conditions, such as, for one month, for two months, for three months, for four months, for five months, for six months or more. The "stable" formulations of the invention retain biological activity equal to or more than 80%, 85%, 90%, 95%, 98%, 99% or 99.5% under given manufacture, preparation, transportation and storage conditions. The stability of said preparation can be assessed by degrees of aggregation, degradation or fragmentation by methods known to those skilled in the art.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di-, or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenthylamine; (trihydroxymethyl) aminoethane; and the like, see, for example, J. Pharm. Sci., 66: 1-19 (1977).

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

Buffers, acids and bases may be incorporated in the compositions to adjust pH. Agents to increase the diffusion distance of agents released from the composition may also be included.

The charge, lipophilicity or hydrophilicity of a composition may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

The specific method used to formulate the novel formulations described herein is not critical to the present invention and can be selected from a physiological buffer (Feigner et al., U.S. Pat. No. 5,589,466 (1996)).

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

The compositions can take the form of solutions, suspensions, emulsions, powders, sustained-release formulations, depots and the like. Examples of suitable carriers are described in "Remington's Pharmaceutical Sciences," Martin. Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium gluconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of biopolymer.

Additional miscellaneous excipients include bulking agents, (e.g., starch), chelating agents (e.g., EDTA), antioxidants (e.g., ascorbic acid, methionine or vitamin E) and cosolvents.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

The instant invention encompasses formulations, such as, liquid formulations having stability at temperatures found in a commercial refrigerator and freezer found in the office of a physician or laboratory, such as from about 20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10%

The formulations to be used for in vivo administration must be sterile. That can be accomplished, for example, by filtration through sterile filtration membranes. For example, the formulations of the present invention may be sterilized by filtration.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, .gamma.-carboxyglutamate, and O-phosphoserine.

The term "amino acid analogs," refers to compounds that have the same basic chemical structure as a naturally occurring amino acid, e.g., an .alpha. carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid Amino acid "mimetics" refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of ordinary skill in the art recognizes that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typical conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The host referred to in the inventive methods can be any host. Preferably, the host is a mammal. As used herein, the term "mammal" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovine (cows) and Swine (pigs) or of the order Perssodactyla, including Equine (horses). It is most preferred that the mammals are of the order Primates, Ceboids, or Simoids (monkeys) or of the order Anthropoids (humans and apes). An especially preferred mammal is the human.

As used herein, "antibody" includes reference to an immunoglobulin molecule immunologically reactive with one or more particular antigens on TGF-β, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab').sub.2, Fab, Fv and rIgG. See also, Pierce Catalog and Handbook, 1994-1995 (Pierce Chemical Co., Rockford, Ill.). See also, e.g., Kuby, J., Immunology, 3.sup.rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of TGF-β, or any portion or fragment which inhibits TGF-β binding the appropriate receptor. Desirably, the antibody is specific for the functional portion of TGF-β, or any portion or fragment which inhibits TGF-β binding the appropriate receptor, such that there is minimal cross-reaction with other peptides or proteins.

Methods of testing antibodies for the ability to bind to any for the functional portion of TGF-β, or any portion or fragment which inhibits TGF-β binding the appropriate receptor are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies to for the functional portion of TGF-β, or any portion or fragment which inhibits TGF-β binding the appropriate receptor of the present invention are known in the art. For instance, standard hybridoma methods are described in, e.g., Kohler and Milstein, Eur. J. Immunol., 5, 511-519 (1976), Harlow and Lane (eds.), Antibodies: A Laboratory Manual, CSH Press (1988), and C. A. Janeway et al. (eds.), Immunobiology, 5th Ed., Garland Publishing, New York, N.Y. (2001)). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3rd Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

The invention also provides antigen binding portions of any of the antibodies described herein. The antigen binding portion can be any portion that has at least one antigen binding site, such as Fab, F(ab')2, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive AAs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

EXAMPLES

Mice.

Mice were purchased C57BL/6J (WT) from the Jackson Laboratory. For SMTS mouse model, the Achilles' tendon was semi-transected to generate a destabilized enthesopathy animal model adjusted by a previously described procedure.[77] Briefly, 3-month-old male mice were anesthetized by ketamine and xylazine followed by semi-transection of Achilles' tendon to induce abnormal mechanical loading-associated enthesopathy on the left calcaneus. Sham operations were done on independent mice. For the dosage screening experiments, 3-month-old sham-operated and SMTS mice were assigned into fourteen groups, with six mice per group. Three days after surgery, different doses (1, 3, 5, 10 mg/kg) of TGF-β-neutralizing antibody (1D11) or the equivalent volume of vehicle antibody (13C4) were injected intraperitoneally three times a week, once a week and once a month for 30 d. All the mice were euthanized two months after surgery (n=10 per group).

For the dorsiflexion immobilization model, TempAssure 0.5 mL PCR tubes (USA Scientific, 1405-8100) were used. The bottoms (15 mm from the bottom) and the caps were removed from the tubes. Two holes were drilled 4 mm from the top of the tube on opposite sides (180 degrees apart). The left ankle of a C57BL/6J (WT) mouse was inserted into the top of the tube in a dorsiflexion position. An iron wire 2 cm in length was utilized to secure the device in place, inserted in the two holes and above the ventral part of the ankle. When this device was applied, the calf muscles of the mice were tight. Therefore, the dorsiflexion of the ankle joint was restricted and the foot was bent into a talipes calcaneus position. The devices were applied on mice for 12 hours every day for 4 or 8 weeks as noted in results. The mice were allowed to move freely in the cages. At the end of each experimental time points, the devices were discarded and mice were sacrificed. Non-immobilized littermates were used as controls.

CED mice were generated in our laboratory as previously described, in which the CED-derived TGF-β1 mutation (H222D) is specifically expressed by osteoblastic cells driven by a 2.3-kb type I collagen promoter (n=10 per group).[26] Nestin-cre™Er mice were purchased from the Jackson Laboratory. Mice with floxed Tgfbr2 (Tgfbr2$^{flox/flox}$) were obtained from the lab of H. L. Moses.[78] Nestin-cre™Er mice were crossed with Tgfbr2$^{flox/flox}$ mice. The offspring were intercrossed to generate Nestin-cre™Er::Tgfbr2$^{flox/flox}$ offspring. Sham or SMTS operations were performed on 3-month-old male Nestin-cre™Er::Tgfbr2$^{flox/flox}$ mice. One day after surgery, mice were treated with either 100 mg per kg body weight of tamoxifen or vehicle three times a week for 4 weeks and euthanized the mice 8 weeks after surgery (n=10 per group). All animals were maintained in the Animal Facility of the Johns Hopkins University School of Medicine. The experimental protocols were reviewed and approved by the Institutional Animal Care and Use Committee of the Johns Hopkins University, Baltimore, Md., USA.

Specimen Collection

Mice were euthanized and perfusion fixed with 10% buffered formalin via the left ventricle for 5 minutes. Then we dissected the ankles with Achilles' tendons and fixed the specimens in 10% buffered formalin for 24 hours, decalcified in 10% ethylenediamine tetraacetic acid (EDTA) (pH 7.0) for 3-4 days and embedded in paraffin, Optimal Cutting Temperature Compound (O.C.T. compound, VWR, 25608-930) or medium containing 8% Gelatin (Sigma-Aldrich, G1890) and 2% Polyvinylpyrrolidone (Sigma-Aldrich, PVP40) at −80° C. The majority of analyses were in paraffin-embedded specimens, while detection of Nestin and CD31 was more optimal in frozen specimens.

Histology and Morphometric Analysis

Blocks were sectioned at 4 μm or 80 μm (for CD31 immunofluorescent staining) intervals using a Microm cryostat (for frozen blocks) or a Paraffin Microtome (for paraffin blocks). The sections being compared were taken at the same anatomical level, to ensure which all following experiments were conducted on serial sections and stained. For frozen tissue sections, slides were embedded in O.C.T compound (for 4-μm thick slide) or gelatin (for 80-μm thick slide) for 10 minutes at −20° C. For paraffin sections, slides were dewaxed in xylene. Both dewaxed paraffin sections and frozen sections were heated to 99° C. for 20 minutes in citrate buffer (10 mM, pH 6.0) for antigen retrieval, and rehydrated. After washing 3 times with PBS, tissue sections were incubated with primary antibodies diluted in blocking solution (10% BSA in PBS) overnight at 4° C. in a humidified chamber. Sections were washed 3 times with Tris-buffered saline and incubated with secondary antibodies in blocking solution for 1 hour at room temperature. All immunofluorescence micrographs were acquired using an Axiovert 200M microscopy system (Carl Zeiss MicroImaging). Images were captured using Velocity software, and quantifications were performed using ImageJ software.

Four-micrometer-thick or eighty-micrometer-thick (for CD31 immunofluorescent staining) sagittal-oriented sections of the Achilles' tendon enthesis were processed for histology and morphometric analysis. 10× images were used to measure the area of the calcified and un-calcified fibrocartilage after H&E and Safranin O and fast green staining. Calcified fibrocartilage (CF) and un-calcified fibrocartilage (UF) were separated by the tidemark line. The area from the interface between UF and Achilles tendon were measured to tidemark as the thickness of UF and the area from tidemark to Posterior Calcaneal Tuberosity (PCT) as the thickness of CF.

Trap staining was processed following the manufacturer's protocol (Sigma-Aldrich, 387A-1KT), followed by counterstaining with Methyl Green (Sigma-Aldrich, M884). Quantitative analysis of osteoclast surface per bone surface was conducted in a blinded fashion with OsteoMeasureXP Software (OsteoMetrics, Inc.).

Immunostaining was performed using a standard protocol. Sections were incubated with primary antibodies to mouse nestin (Ayes Labs, Inc., 1:300, lot NES0407), osterix (Abcam, 1:600, ab22552), pSmad2/3 (Santa Cruz Biotechnology Inc., 1:50, sc-11769), CD31 (Abcam, 1:100, ab28364), MMP13 (Abcam, 1:40, ab3208), collagen X (Abcam, 1:80, ab58632) overnight at 4° C. For immunohistochemical staining, a horse radish peroxidase-streptavidin detection system (Dako), was used to detect the immunoactivity, followed by counterstaining with hematoxylin (Sigma-Aldrich, H9627). For immunofluorescence staining, secondary antibodies conjugated with red fluorescence was used. The antibodies were incubated while avoiding light at room temperature for 1 h and mounted on slides with ProLong Gold Mounting Reagent with DAPI (P36935, Life Technologies). Sections were then photographed to perform histomorphometric measurements on the entire area of Achilles' tendon enthesis (Olympus DP71). The Quantitative analysis was conducted in a blinded fashion with OsteoMeasureXP Software (OsteoMetrics, Inc.).

Serum TGF-β1 Analysis

The concentration of active TGF-β1 was determined in the mouse serum using the ELISA Development kit (R&D Systems, MB100B) under the manufacturer's instructions. For total TGF-β1 measurement, samples were first treated with 1N HCl (1 μl/50 μl supernatant) for 15 min at room temperature and were neutralized with an equal amount of 1N NaOH before analysis in the ELISA. For active TGF-β1 measurement, samples were analyzed in the ELISA without acid treatment.

MicroCT Analysis

Ankles with feet and Achilles' tendons were dissected free of surrounding tissue from mice, then fixed overnight in 10% formalin and analyzed by high-resolution μCT (Skyscan1172). The images were reconstructed and analyzed by NRecon v1.6 and CTAn v1.9, respectively. The parameters were analyzed using three-dimensional model visualization software, CTVol v2.0. The scanner was set at a voltage of 60 kV and a resolution of 5.78 μm per pixel. Images of PCT were used to perform three-dimensional histomorphometric analyses. The region of interest was defined to cover the whole PCT compartment (from the posterior tip of the calcaneus to 1 mm anterior to the posterior tip of calcaneus). A total of eight consecutive images were used for three-dimensional reconstruction. Three-dimensional structural parameters analyzed included: TV, Tb.Th, Tb.Pf.

CT-Based Microangiography

Angiography of microphil-perfused bones was performed to image blood vessels in bone. Briefly, after the mice were euthanized, the vascular system was flushed with 0.9% normal saline solution containing heparin sodium (100 U/ml) through a needle inserted into the left ventricle followed by fixation with 10% neutral buffered formalin. After 3 times washing using 0.9% normal saline solution, radiopaque silicone rubber compound containing lead chromate (Microfil MV-122, Flow Tech) was then injected. Specimens were stored at 4° C. overnight for contrast agent polymerization. Ankles with feet were then dissected and soaked in 10% neutral buffered formalin for 4 d followed by decalcification in a formic acid-based solution (Cal-Ex II) for 48 h to facilitate image threshold of the vasculature from the surrounding tissues. A high-resolution micro-CT imaging system (Skyscan 1172) was employed to acquire images. The scanner was set at a voltage of 60 kV and a resolution of 5.78 μm per pixel.

Statistics

All statistical analyses were carried out using SPSS 15 software. Data are presented as the mean±SEM. Comparisons were performed using by student t-test (for comparison of WT and CED mice) or One-Way ANOVA, followed by Tukey's post-hoc test (for all the other comparisons) to determine significance between groups. The level of significance was set at P<0.05.

Example 1

Figure 1B:
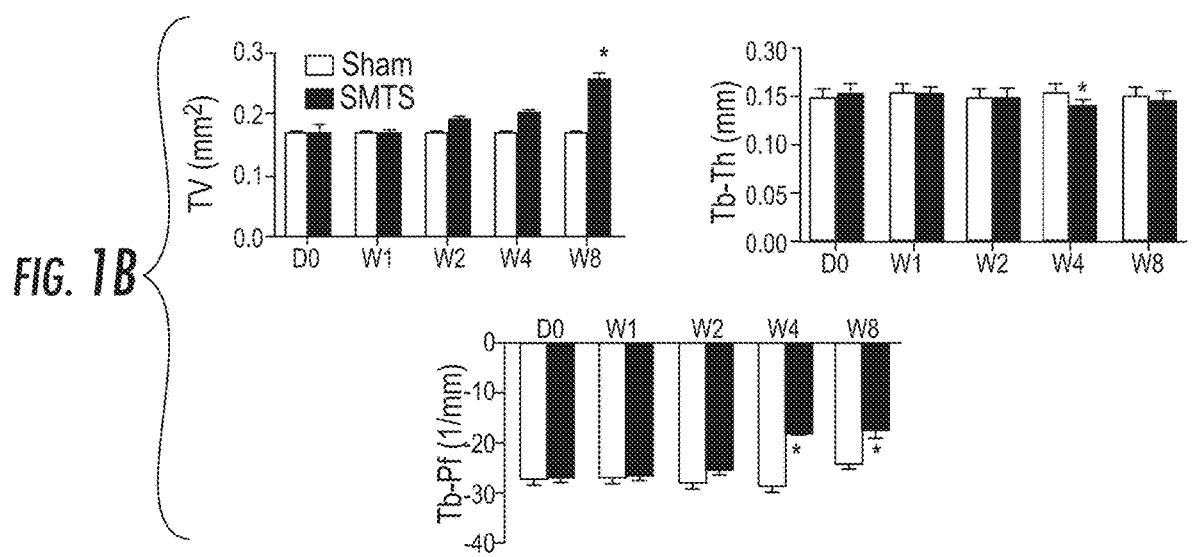
Figure 1C:
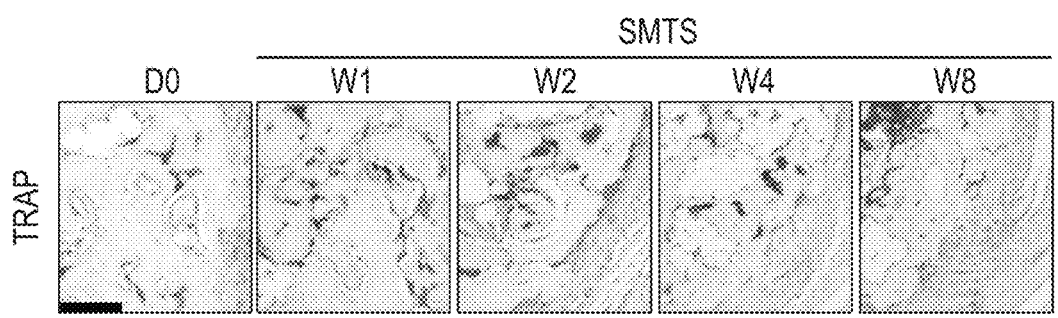
Figure 1D:
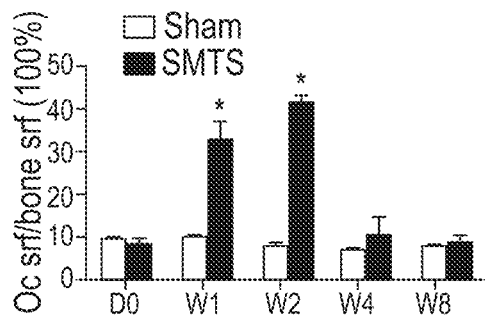
Figure 1E:
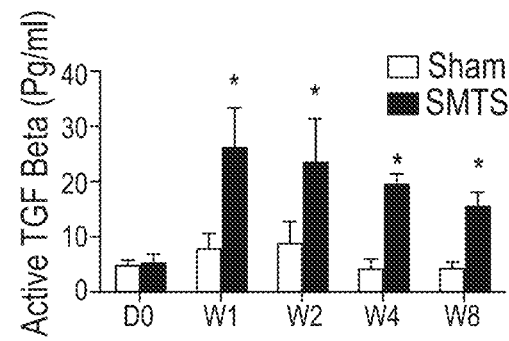
Figure 1F:
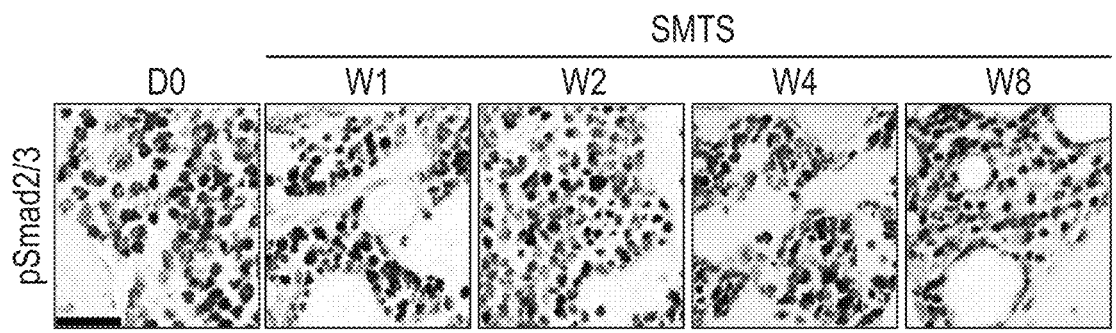
Figure 1G:
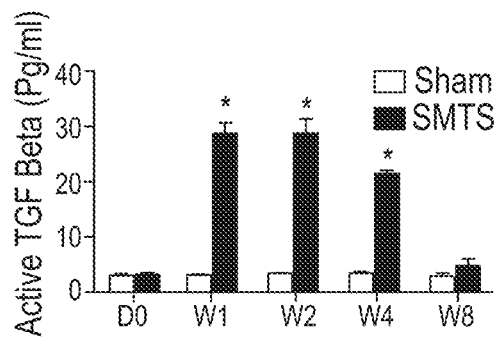

Upregulated TGF-β Activities in Posterior Calcaneal Tuberosity in Achilles' Tendon Enthesopathy Mouse Models To examine the changes at the onset of enthesopathy, Achilles' tendon in 3-month-old male mice were partially transected, termed semi-transection (SMTS) to generate a destabilized Achilles' enthesopathy mouse model. The bone volume in the Posterior Calcaneal Tuberosity (PCT), the site of Achilles' tendon attachment to calcaneus, changed significantly in SMTS mice compared to the sham group as determined by three-dimensional microcomputed tomography (μCT) analysis 4 weeks after surgery (FIGS. 1a, 1b). The thickness of the PCT trabecular bone (Tb.Th) varied in the SMTS group after surgery, with tissue volume (TV) substantially higher by 8 weeks (FIG. 1b). Enthesophyte-like structures were present in 4 of 10 mice 8 weeks after SMTS (FIG. 1a—arrows). A dramatically higher trabecular pattern factor (Tb.Pf), a quantitative parameter of the connectiveness and microarchitecture of trabecular bone,[34] was noted in the SMTS mice compared to sham controls indicating uncoupled bone remodeling (FIG. 1b). TRAP staining showed that the osteoclast surface per bone surface increased in PCT trabecular bone 1 and 2 weeks after surgery. TRAP staining was back to normal levels on week 4 post-surgery while leaving large bone marrow cavities (FIGS. 1c, 1d). A significantly higher active TGF-β concentration in serum was seen in the SMTS mice relative to sham-operated mice from 1 to 8 weeks post-surgery (FIG. 1e), consistent with previous studies reporting higher TGF-β after trauma.[35-38] The total serum TGF-β levels did not change significantly (data not shown) Immunostaining further demonstrated that the number of cells positive for phosphorylated Smad2/3 (pSmad2/3+), a downstream signal of TGF-β, was higher in bone marrow 2 and 4 weeks after surgery as compared to sham controls (FIGS. 1f, 1g). These results suggest that altered mechanical loading induces PCT trabecular bone resorption, elevating active TGF-β concentrations in these regions and in whole blood. A second Achilles enthesopathy model was also created, termed the Dorsiflexion Immobilization (DI) model, where the ankles of mice were fixed in a dorsiflexion position to mimic overuse of Achilles tendons. Micro CT, TRAP, and pSmad2/3 staining results all showed similar changes compared to the SMTS model (FIGS. 7a-7f).

Example 2

Over-Expression of Active TGF-β in Bone Induces Enthesopathy

Figure 2A:
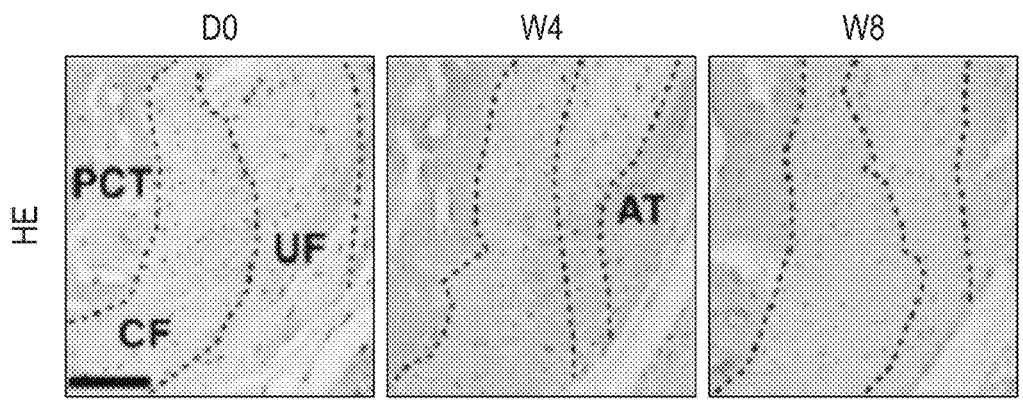
FIGS. 2A-2G illustrate that fibrocartilage displays mineralization in Achilles' tendon enthesis. 2a) H&E staining of Achilles' tendon enthesis. The PCT bone, CF and UF are separated by dotted lines. AT, Achilles' Tendon. Scale bar, 200 μm. (2b) Quantitative analysis of area of CF and UF. (c) Safranin O and Fast Green (SOFG) staining of Achilles tendon enthesis compartment, proteoglycan (red), bone (green) and Achilles tendon (green). Black arrows indicate direct connection between bone marrow and calcified fibrocartilage. Black open arrow indicates blood vessel invasion from PCT bone to calcified fibrocartilage. Scale bar, 200 μm. (2d, 2f) Immunohistochemical and (2e, 2g) quantitative analysis of (2d, 2e) COLX+ cells and (f, g) MMP13+ cells (bottom) in fibrocartilage of mouse Achilles tendon enthesis after SMTS surgery. Dotted lines separate UF and CF. Scale bars, 150 μm. D0, prior to SMTS surgery. W1, one week after SMTS surgery; W2, two weeks after SMTS surgery; W4, four weeks after SMTS surgery; W8, eight weeks after SMTS surgery. Data shown as Mean±SEM. n=10. *P<0.05 compared to the D0 group or between groups.
Figure 2B:
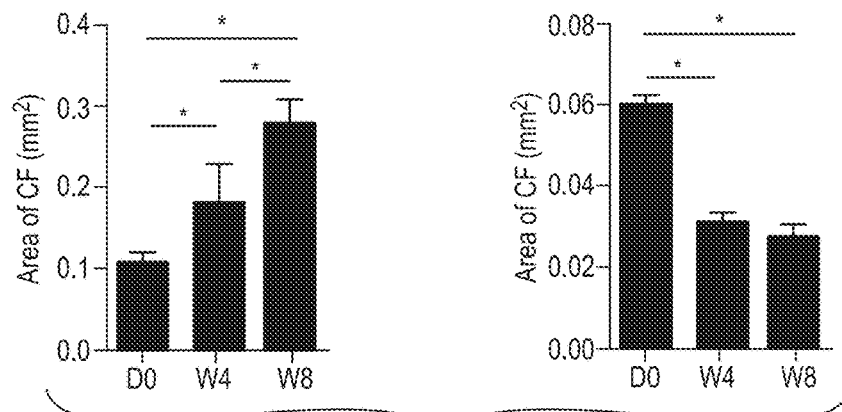
Figure 2C:
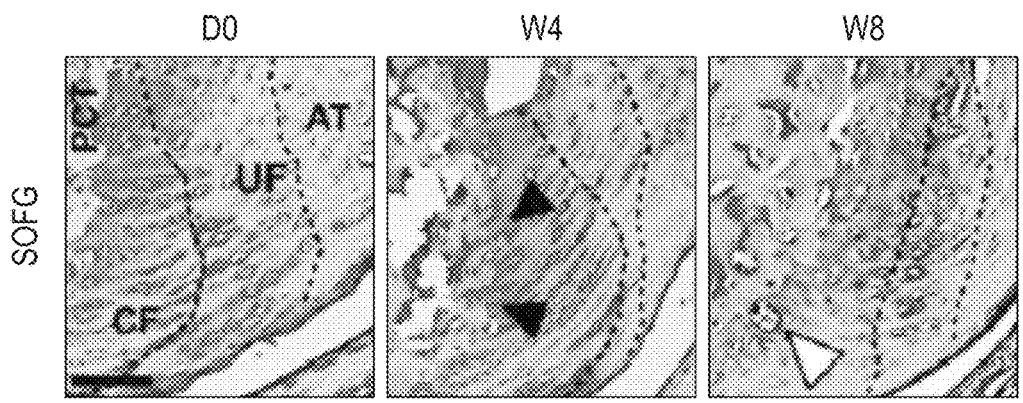
Figure 2D:
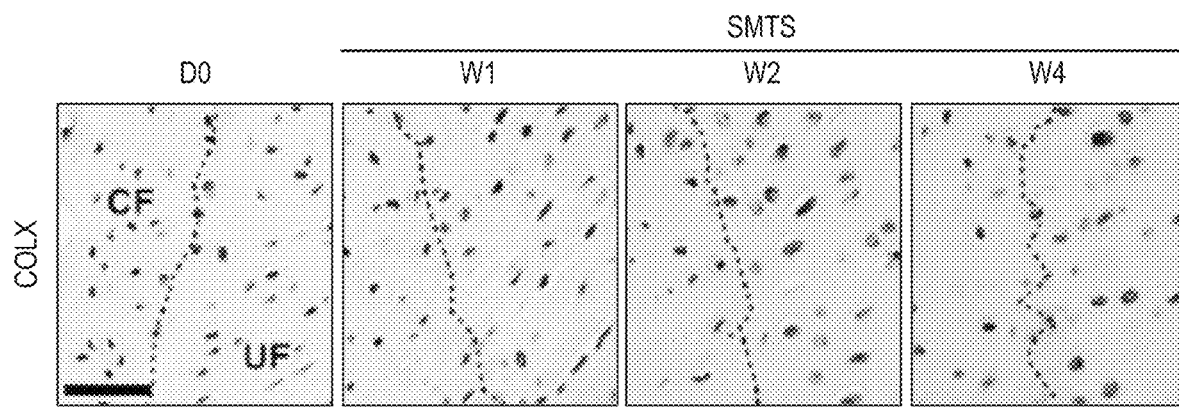
Figure 2E:
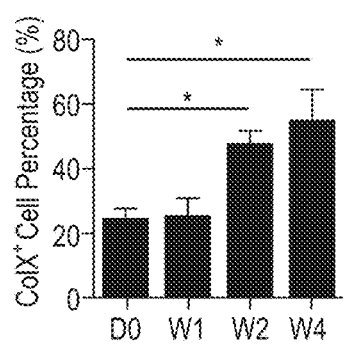
Figure 2G:
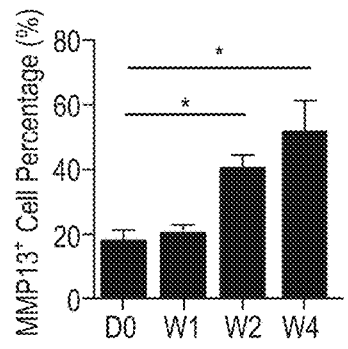
Figure 2F:
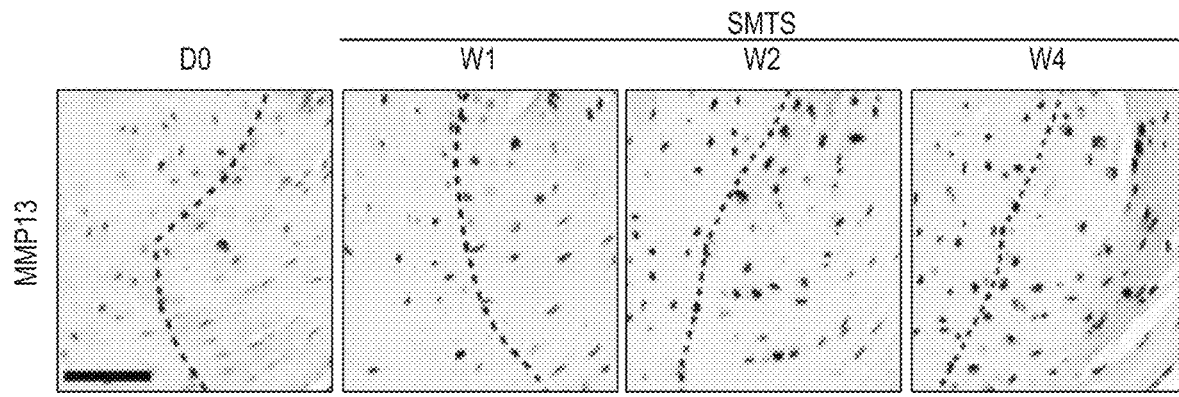

The fibrocartilage of Achilles' tendon enthesis was examined after SMTS. H&E staining showed the area of Calcified Fibrocartilage (CF) increased and Un-calcified Fibrocartilage (UF) decreased in SMTS mice 4 and 8 weeks after surgery compared to those in age and gender-matched sham-operated mice with the tidemark moving closer to the interface between UF and Achilles tendon (FIGS. 2a, 2b). Proteoglycan decreased in UF in the SMTS mice both 4 and 8 weeks after surgery (FIG. 2c). Moreover, bone marrow directly linked to CF by 4 weeks, with blood vessel invasion noted into CF in mice 8 weeks after SMTS surgery (FIG. 2c). We also observed elevated concentrations of type X collagen (COLX) (FIGS. 2d, 2e) and Matrix Metallopeptidase 13 (MMP13) (FIGS. 2f, 2g) in fibrocartilage in SMTS mice as compared to sham controls, suggesting the process of calcification and degeneration.[39,40] The DI mouse model also revealed similar results (FIGS. 8a-8f). These results suggest that unbalanced mechanical loading induce fibrocartilage mineralization in Achilles tendon enthesis.

Example 3

Over-Expression of Active TGF-β in Bone Induces Enthesopathy

Figure 3E:
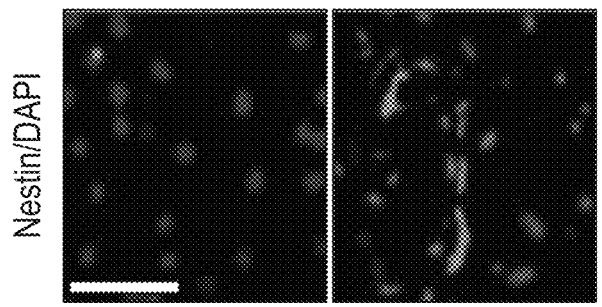
Figure 3F:
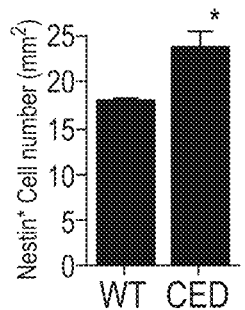
Figure 3G:
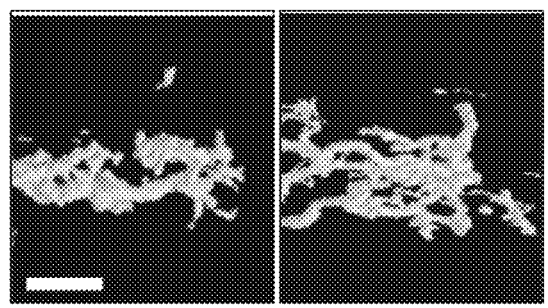
Figure 3H:
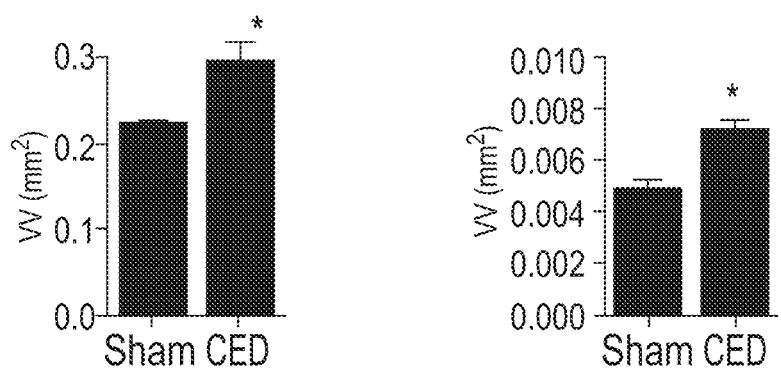

In Camurati-Engelmann disease (CED), active TGF-β1 is increased due to mutations in its prodomain.[41] Previously a CED mouse model was generated where active TGF-β1 is overexpressed by type I collagen promoter resulting in high active TGF-β1 concentrations in the bone marrow.[31] Our CED mouse model was therefore utilized to determine whether high concentrations of active TGF-β1 initiate enthesopathy. We detected significantly higher pSmad2/3+ expression in fibrocartilage in the Achilles' tendon enthesis of CED mice (FIGS. 3a, 3b). Micro CT images showed disrupted bone formation with an enthesophyte-like structure at the Achilles' tendon enthesis in CED mice relative to wild-type (WT) littermates (FIG. 3c). Quantitative analysis of μCT data of CED mice was similar to SMTS and DI mice with increased TV and Tb.Pf while decreased PCT Tb.Th than WT controls (FIG. 3d). Nestin+ cells have been shown to represent a subset of bone marrow precursor cells that in postnatal bones can differentiate into endothelial cells and mesenchymal lineage cells.[42-44] Immunostaining for Nestin revealed a significantly higher number of Nestin+ cells in the calcaneal bone marrow of CED mice compared to WT littermates (FIGS. 3e, 3f). Once committed to the endothelial lineage, Nestin+ cells are involved in vessel formation.[44] Angiogenesis analysis utilizing microfil contrast-enhanced angiography revealed that the vessel volume and number of blood vessels in PCT bone marrow were significantly higher in CED mice compared to wide type controls (FIGS. 3g, 3h). The number of osterix positive (Osx+) osteoprogenitors was also significantly higher in the PCT bone marrow of CED mice compared to WT controls (FIGS. 3i, 3j), indicating that increased osteoblastic differentiation likely contributed to de novo bone formation. We found the area of the CF layer was greater in the CED mice, whereas the UF area was less (FIGS. 3k, 3l). Compared to WT littermates, there was also significantly lower proteoglycan expression at the CF and UF zone in the CED mice (FIG. 3m). Altogether, CED mice have an enthesopathy phenotype similar to SMTS and DI mouse models, suggesting that high concentrations of active TGF-β1-induced abnormal bone formation and vessel formation, contributing to Achilles' tendon enthesopathy.

Example 4

Systemic Injection of TGF-β1 Antibody Attenuates Progression of Enthesopathy

Figure 4A:
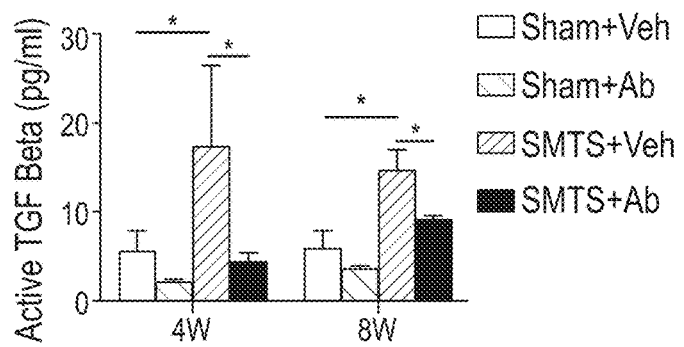
FIGS. 4A-4E show that systemic injection of TGFβ1 antibody maintains Achilles' tendon enthesis structure and reduces the unregulated TGFβ signaling. (4a) Quantitative analysis of active TGFβ in peripheral serum of antibody (1D11) or vehicle (13C4) treated mice 4 or 8 weeks after sham or SMTS operation by ELISA. (4b, 4d) Immunohistochemical and (4c, 4e) quantitative analysis of pSmad2/3+ cells (brown) in mouse (4b, 4c) Achilles tendon enthesis fibrocartilage and (4d, 4e) PCT bone. Scar bar, 50 μm. (4f) μCT images of the PCT (sagittal view) of mice treated with 5 mg per kg body weight of the TGFβ1 neutralizing antibody 1D11 weekly for 30 days and analyzed 4 or 8 weeks after SMTS or sham surgery. Scale bar, 500 μm. (4g) Quantitative analysis of TV, Tb.Th and Tb.Pf in PCT determined by μCT analysis. (4h) Immunostaining and (4i) quantitative analysis of Nestin+ cells (red) in the PCT bone marrow. Scale bar, 30 μm. (4j) Immunostaining of CD31+ (red) vessels and the (4k) quantification of the number of vessels positive for CD31 (per $mm^2$). Scale bar, 100 μm. (4l) Osx+ cells (brown) in the PCT bone marrow and (4m) quantifications. 4 W, four weeks after SMTS surgery; 8 W, eight weeks after SMTS surgery. Data shown as Mean±SEM. n=10. *P<0.05 compared between groups or to the sham group.
Figure 4B:
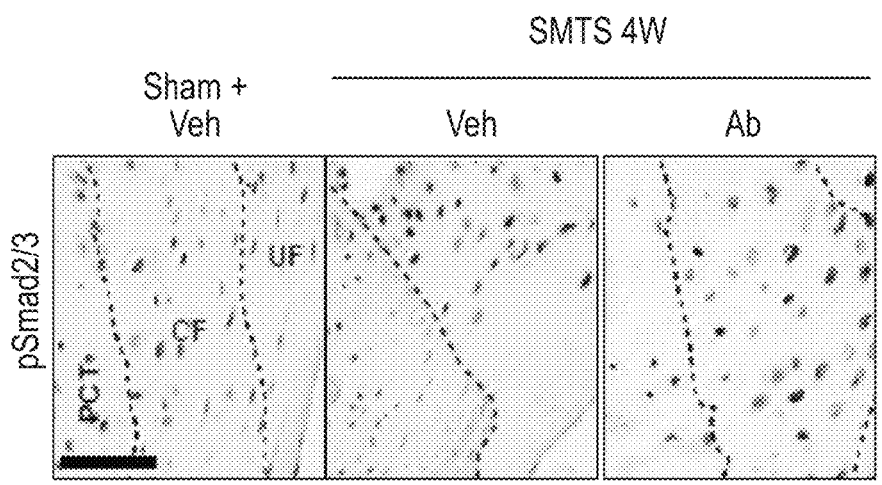
Figure 4C:
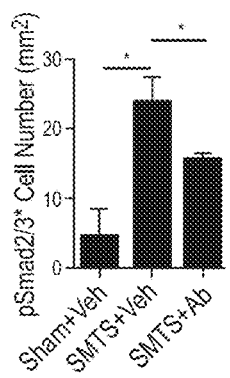
Figure 4D:
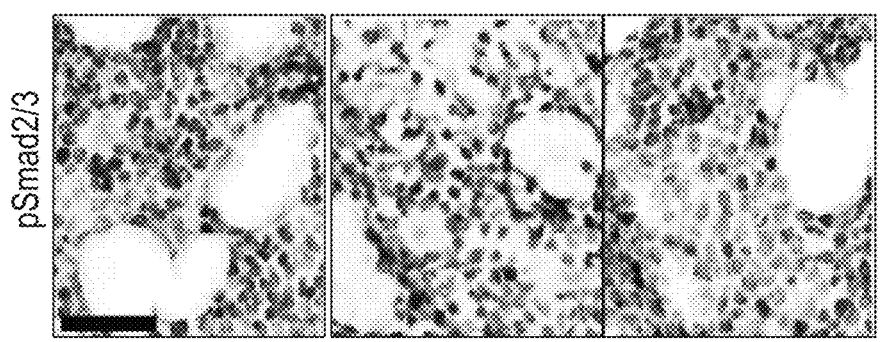
Figure 4E:
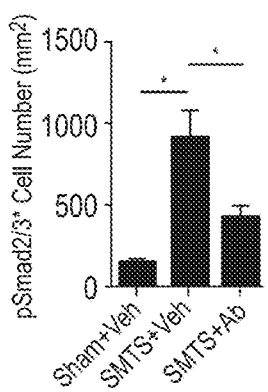
Figure 9A:
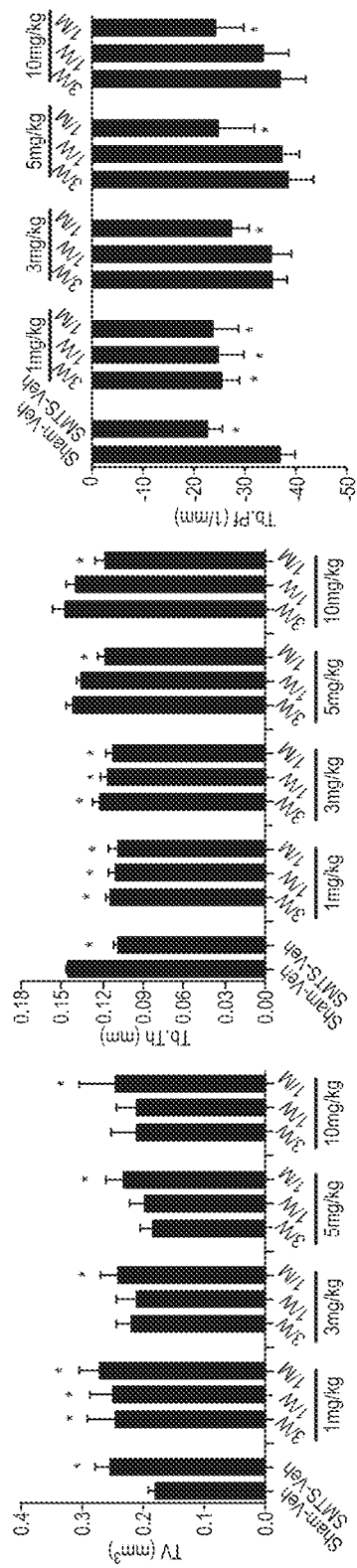
FIGS. 9A-9B show the dosage of TGF-β antibody is optimized by screening experiments. (9a) Quantitative analysis of TV, Tb.Th and Tb.Pf in PCT determined by μCT analysis of sham or SMTS operated mice treated with different doses (1, 3, 5, 10 mg/kg) of TGF-β antibody (1D11)
Figure 9B:
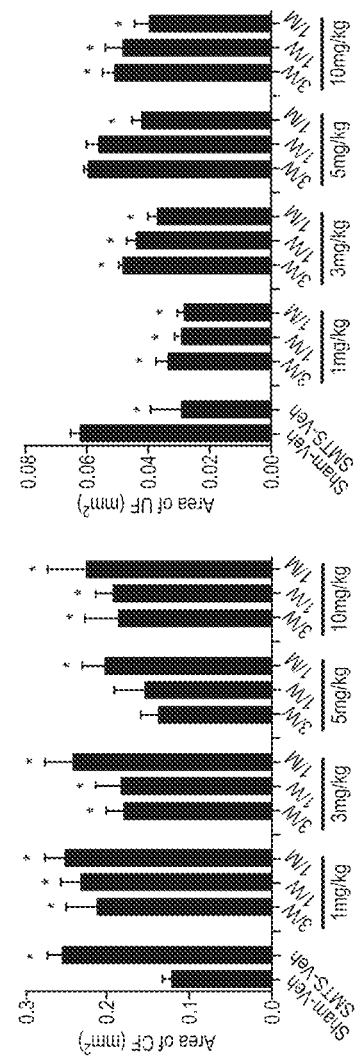

As SMTS, DI, and CED mice showed similar pathological changes, we utilized the SMTS model only for the following experiments. Injection of a TGF-β1 neutralizing antibody (1D11) has been shown to rescue uncoupled bone formation induced by high concentrations of active TGF- β1.³⁰ We therefore investigated the effects of TGF-β1 inhibition on enthesopathy pathogenesis. First, different doses of 1D11 were screened in experimental mice to identify the optimal dose and injection frequency, which was about 5 mg per kg body weight injected weekly (FIGS. 9a, 9b). Vehicle antibody (13C4) consisted of an identical IgG complex lacking any TGF-β-binding capabilities. 1D11 significantly decreased the concentration of active TGF-β in whole blood in SMTS mice relative to vehicle (FIG. 4a). TGF-β signaling was also reduced at the tissue level as demonstrated by immunostaining of cells positive for pSmad2/3 in the fibrocartilage in Achilles tendon enthesis (FIGS. 4b, 4c) as well as in the PCT bone marrow in SMTS mice in the SMTS 1D11-treated mice relative to SMTS vehicle-treated mice (FIGS. 4d, 4e). Micro CT analysis of the PCT in SMTS mice demonstrated decreased PCT bone TV, increased Tb.Th, and lowered Tb.Pf relative to vehicle-treated SMTS mice (FIG. 4l). There was no statistically significant difference in these parameters comparing the SMTS 1D11-treated mice relative to the controls, sham-operated mice treated with either vehicle or 1D11, demonstrating restoration of trabeculae connectivity and microarchitecture (FIG. 4g). The increase in Nestin⁺ cells observed in the SMTS mice relative to sham surgery controls was attenuated by 1D11 (FIGS. 4h, 4i). Similarly, the number of CD31⁺ vessels, a marker of endothelial cells, was also significantly higher in the PCT bone marrow of SMTS mice relative to sham surgery controls, and this effect was reduced by 1D11 treatment (FIGS. 4j, 4k). Injection of 1D11 significantly decreased Osx⁺ cell numbers in SMTS mice relative to vehicle. Furthermore, Osx⁺ cells were noted largely in the bone marrow of SMTS vehicle treated mice, whereas the Osx⁺ cells in the SMTS 1D11 mice were largely located on the bone surface, similar to Sham-operated controls (FIGS. 4l, 4m). Collectively, these results indicate that inhibition of TGF-β signaling can decrease the number of Nestin⁺ cells that may contribute to osteogenesis and vessel formation.

Example 5

TGF-β Antibody Attenuates Fibrocartilage Destruction in Enthesopathy

Figure 5A:
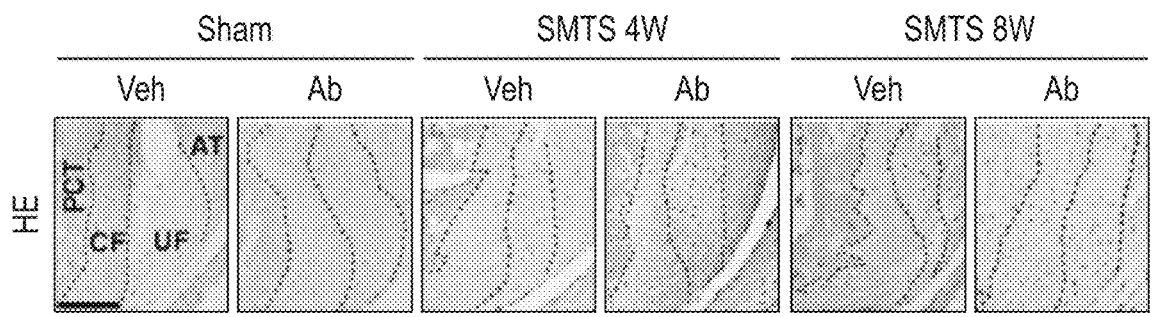
Figure 5B:
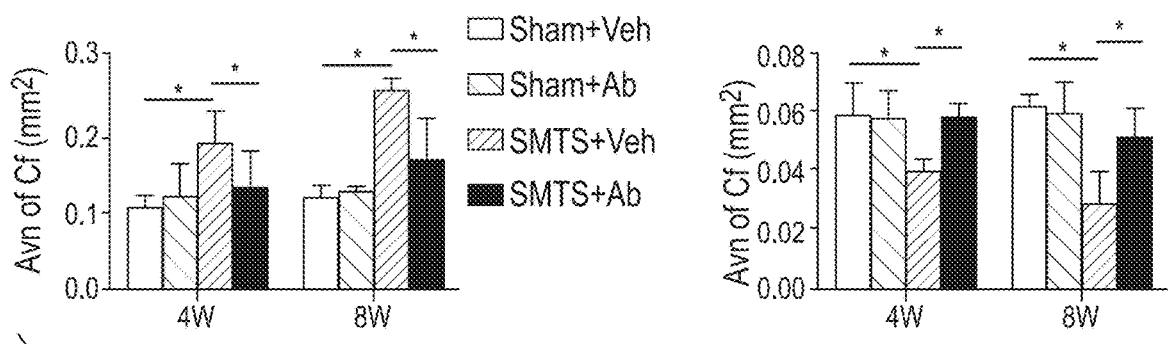
Figure 5C:
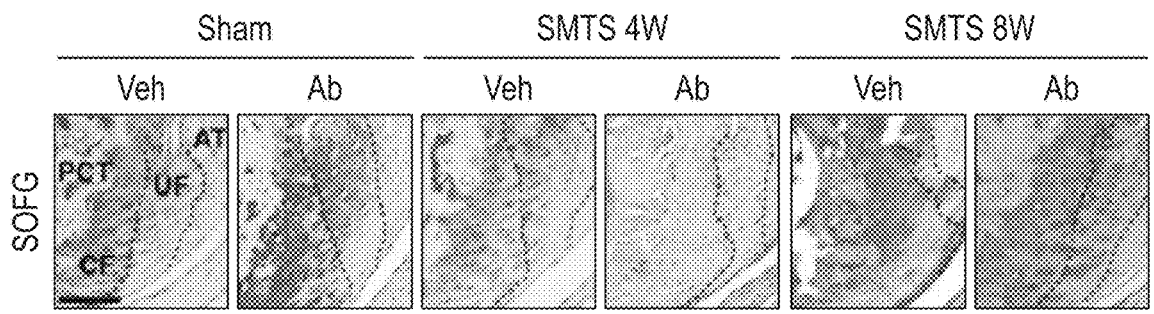
Figure 7A:
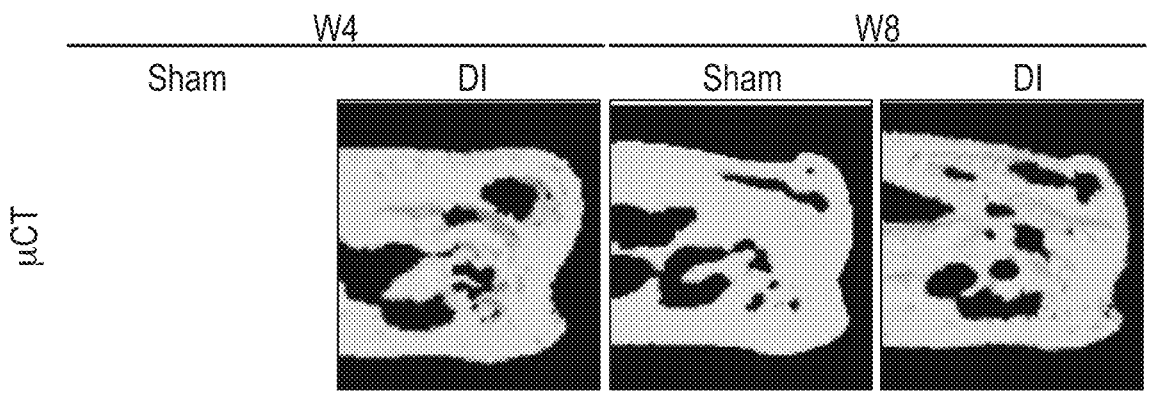
FIGS. 7A-7F (S3) show upregulated TGFβ signaling is associated with enthesopathy in DI mice. (7a) Micro CT images of the PCT (sagittal view). Scale bar, 500 μm. (7b) Quantitative analysis of TV, Tb.Th and Tb.Pf in PCT determined by μCT analysis. (7c) TRAP staining (magenta) in mouse PCT bone marrow. Scale bar, 200 μm. (7d) Quantitative analysis of TRAP+ osteoclast surface (Oc.srf) per Bone Surface (Bone Srf). (7e) Immunofluorescent staining of pSmad2/3+ cells (red) in mouse PCT bone marrow. Scale bar, 200 μm. (7f) Quantitative analysis of the number of pSmad2/3+ cells per bone marrow area ($mm^2$).B, Bone; BM, bone marrow. W4, four weeks after DI; W8, eight weeks after DI. Data shown as Mean±SEM. n=10. *P<0.05 compared to the sham group.
Figure 7B:
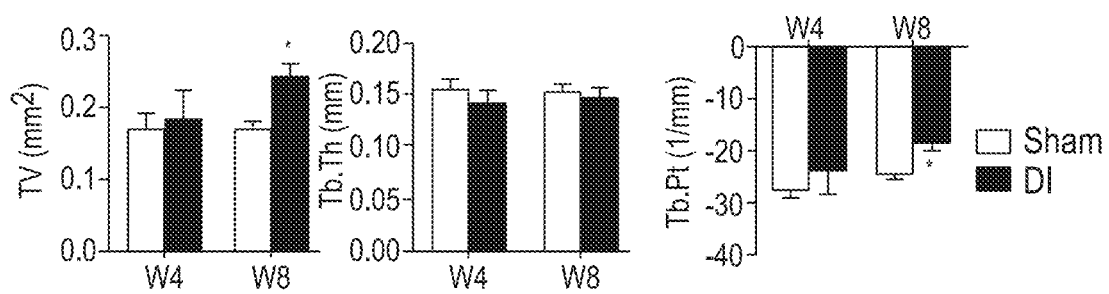
Figure 7C:
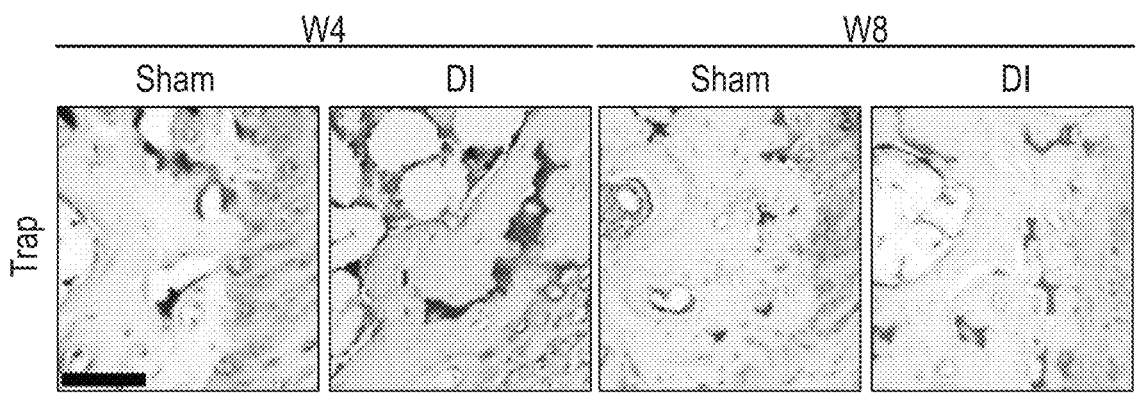
Figure 7D:
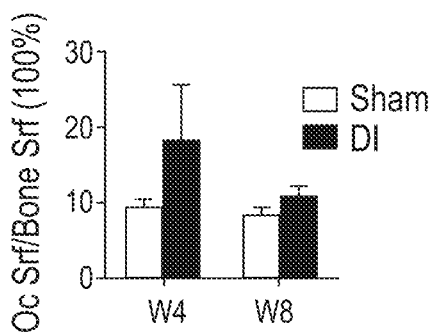
Figure 7E:
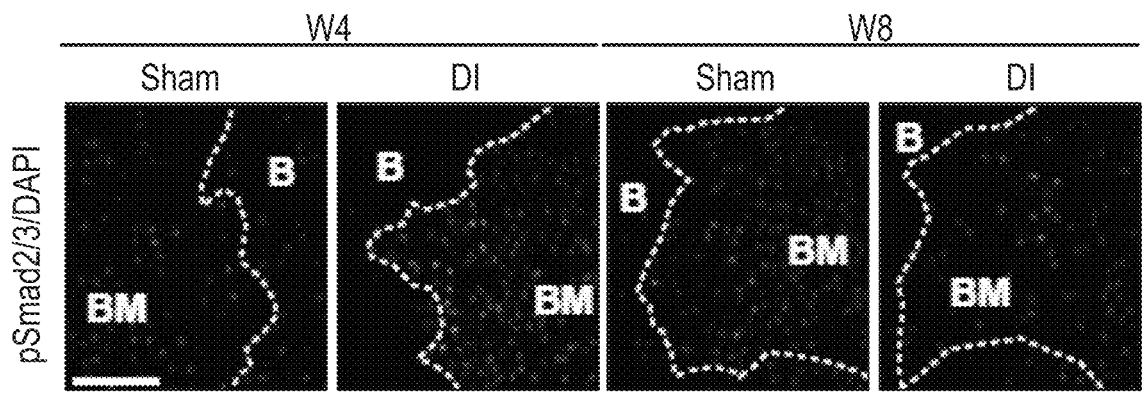
Figure 7F:
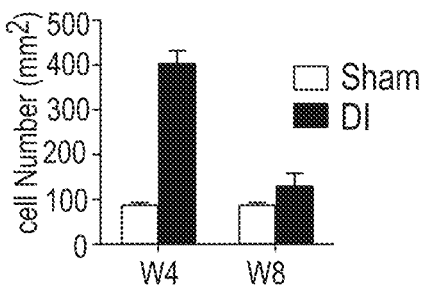
Figure 8A:
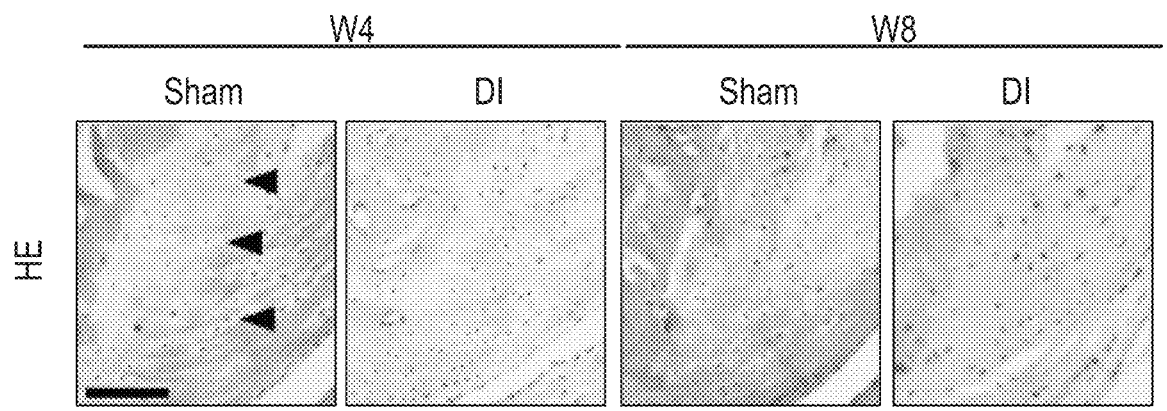
FIGS. 8A-8F (S4) depict fibrocartilage displaying mineralization in Achilles' tendon enthesis. (8a) H&E staining of Achilles' tendon enthesis. Black triangles indicate tide mark. To better illustrate tide marks, we used dotted lines in main figures. Scale bar, 200 μm. (8b) Quantitative analysis of area of CF and UF. (8c, 8e) Immunohistochemical and (8d, 8f) quantitative analysis of (8c, 8d) COLX+ cells and (8e, 8f) MMP13+ cells (bottom) in fibrocartilage of mouse Achilles' tendon enthesis after SMTS surgery. Black triangles indicate tide mark. Scale bars, 150 μm. D0, prior to SMTS surgery; W2, two weeks after SMTS surgery; W4, four weeks after SMTS surgery; W8, eight weeks after SMTS surgery. Data shown as Mean±SEM. n=10. *P<0.05 compared to the sham or D0 group.
Figure 8B:
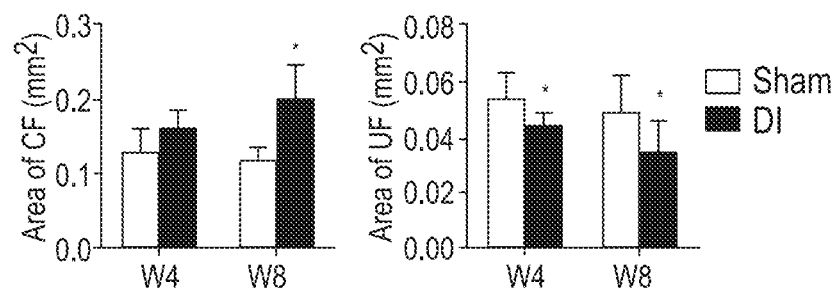
Figure 8C:
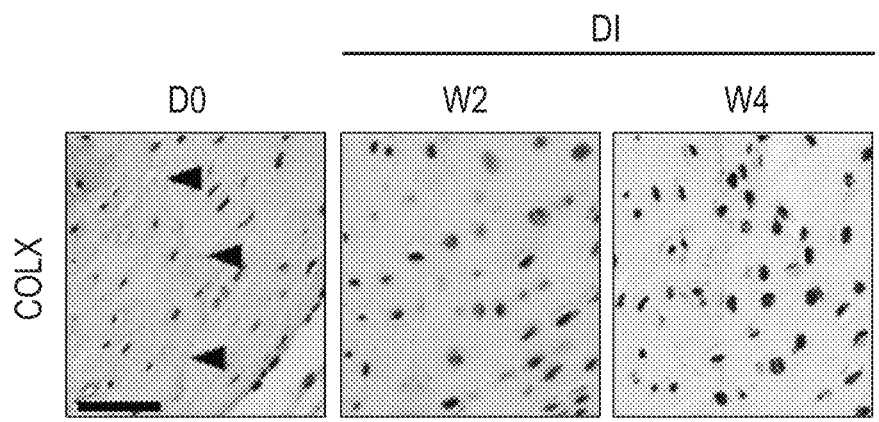
Figure 8D:
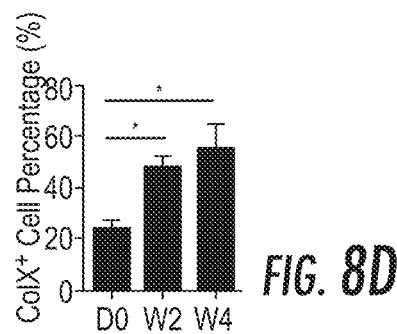
Figure 8E:
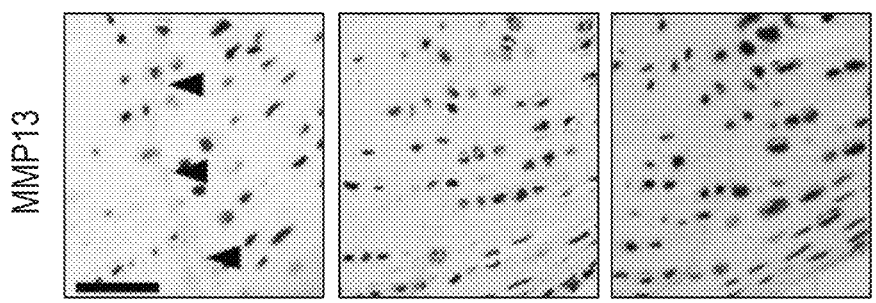
Figure 8F:
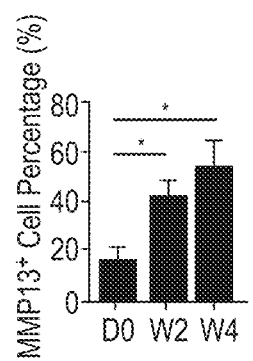

As the PCT bone phenotype was improved with 1D11 in the SMTS mice, we next evaluated the effect of 1D11 on the enthesis. The changes in the area of CF and UF caused by SMTS were restored in SMTS 1D11 mice relative to sham-operated mice as revealed by H&E staining (FIGS. 5a, 5b). The 1D11 also improved proteoglycan staining after SMTS operation compared to vehicle treated mice (FIG. 5c). Furthermore, 1D11 also attenuated the elevated expression of MMP13 or type X collagen in fibrocartilage as compared to SMTS vehicle treatment (FIGS. 5d-5g). Collectively, these results indicate that systemic inhibition of TGF-β1 activity maintained enthesis and fibrocartilage structure.

Example 6

Genetic Knockout Tgfbr2 in MSCs Prevents Enthesopathy

To determine if the changes of the enthesis was the sequela of elevated MSCs by high levels of bone marrow TGF-β signaling events, an inducible mouse model genetically targeting TGF-β signaling in Nestin+ cells was employed. We injected Nestin-creTMEr::Tgfbr2flox/flox mice with tamoxifen to specifically delete Tgfbr2 (Tgfbr2−/−) in the Nestin+ cells. TGF-β binds to type II TGF-β receptor (Tgfbr2) and to type I TGF-β receptor (Tgfbr1) complex to induce phosphorylation of downstream Smad2/3. Deletion of Tgfbr2 blocks the TGF-β signaling cascade. The microstructure of the PCT was maintained and enthesophytes were not noted in Tgfbr2−/− mice while evident in control SMTS Tgfbr2f/f mice (FIG. 6a). At 4 weeks, the SMTS Tgfbr2−/− mice showed improvement in Tb.Th and Tb.Pf relative to SMTS Tgfbr2f/f mice. At 8 weeks, TV and Tb.Pf were increased while Tb.Th was decreased in SMTS Tgfbr2f/f mice relative to Sham controls. There were no statistical differences in Tb.Th or Tb.Pf between SMTS Tgfbr2−/− mice at 8 weeks relative to any other treatment group, suggesting an attenuated phenotype in SMTS Tgfbr2−/− mice (FIG. 6b). The number of Nestin+ cells and Osx+ osteoprogenitors in the PCT bone marrow of SMTS Tgfbr2−/− mice were decreased and the Osx+ cells resided primarily on the bone surface compared to SMTS Tgfbr2f/f littermates (FIGS. 6c-6f). Angiography analyses demonstrated that the number of blood vessels and vessel volume in PCT of SMTS Tgfbr2f/f mice were significantly higher relative to sham surgery controls and SMTS Tgbfr2−/− mice (FIGS. 6g, 6h). Deletion of Tgbfr2 in Nestin lineage cells was sufficient to prevent the change in area observed in CF and UF in SMTS mice (FIGS. 6i, 6j). Less proteoglycan loss in fibrocartilage was also noted in the SMTS Tgfbr2−/− mice as compared to in the SMTS Tgfbr2f/f mice (FIG. 6k) Immunostaining revealed that the expression of MMP13 and type X collagen was significantly attenuated in SMTS Tgfbr2−/− mice compared to SMTS Tgfbr2f/f littermates, indicating the inhibition of fibrocartilage degeneration and mineralization (FIGS. 6l-6o). These data confirm that high concentrations of active TGF-β contribute to the pathogenesis of Achilles' tendon enthesopathy, which can be partially prevented by inhibition of TGF-β signaling in MSCs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Genin, G. M., et al. Functional grading of mineral and collagen in the attachment of tendon to bone. *Biophysical journal* 97, 976-985 (2009).
2. Benjamin, M., et al. Where tendons and ligaments meet bone: attachment sites ('entheses') in relation to exercise and/or mechanical load. *Journal of anatomy* 208, 471-490 (2006).
3. Ristolainen, L., Kettunen, J. A., Kujala, U. M. & Heinonen, A. Sport injuries as the main cause of sport career termination among Finnish top-level athletes. *Eur J Sport Sci* 12, 274-282 (2012).
4. Jarvinen, T. A., Kannus, P., Maffulli, N. & Khan, K. M. Achilles tendon disorders: etiology and epidemiology. *Foot and ankle clinics* 10, 255-266 (2005).
5. Jozsa, L. & Kannus, P. Histopathological findings in spontaneous tendon ruptures. *Scandinavian journal of medicine & science in sports* 7, 113-118 (1997).
6. Lee, K. S. Musculoskeletal sonography of the tendon. *Journal of ultrasound in medicine: official journal of the American Institute of Ultrasound in Medicine* 31, 1879-1884 (2012).
7. Benjamin, M. & McGonagle, D. The anatomical basis for disease localisation in seronegative spondyloarthropathy at entheses and related sites. *Journal of anatomy* 199, 503-526 (2001).
8. Hibino, N., et al. Callus formation during healing of the repaired tendon-bone junction. A rat experimental model. *The Journal of bone and joint surgery. British volume* 89, 1539-1544 (2007).
9. Raspanti, M., et al. Structure and ultrastructure of the bone/ligament junction. *Italian journal of anatomy and embryology=Archivio italiano di anatomia ed embriologia* 101, 97-105 (1996).
10. McGonagle, D., et al. Histological assessment of the early enthesitis lesion in spondyloarthropathy. *Annals of the rheumatic diseases* 61, 534-537 (2002).
11. Mariotti, V., Facchini, F. & Belcastro, M. G. Enthesopathies—proposal of a standardized scoring method and applications. *Collegium antropologicum* 28, 145-159 (2004).
12. Havelková, P. & Villotte, S. Enthesopathies: Test of Reproducibility of the New Scoring System Based on Current Medical Data. *Slovenská antropologia* 10, 51-57 (2007).
13. Kumagai, J., Sarkar, K., Uhthoff, H. K., Okawara, Y. & Ooshima, A. Immunohistochemical distribution of type I, II and III collagens in the rabbit supraspinatus tendon insertion. *Journal of anatomy* 185 (Pt 2), 279-284 (1994).
14. Sagarriga Visconti, C., Kavalkovich, K., Wu, J. & Niyibizi, C. Biochemical analysis of collagens at the ligament-bone interface reveals presence of cartilage-specific collagens. *Archives of biochemistry and biophysics* 328, 135-142 (1996).
15. Fukuta, S., Oyama, M., Kavalkovich, K., Fu, F. H. & Niyibizi, C. Identification of types II, IX and X collagens at the insertion site of the bovine achilles tendon. *Matrix biology: journal of the International Society for Matrix Biology* 17, 65-73 (1998).
16. Waggett, A. D., Ralphs, J. R., Kwan, A. P., Woodnutt, D. & Benjamin, M. Characterization of collagens and proteoglycans at the insertion of the human Achilles tendon. *Matrix biology: journal of the International Society for Matrix Biology* 16, 457-470 (1998).
17. Thomopoulos, S., Williams, G. R., Gimbel, J. A., Favata, M. & Soslowsky, L. J. Variation of biomechanical, structural, and compositional properties along the tendon to bone insertion site. *Journal of orthopaedic research: official publication of the Orthopaedic Research Society* 21, 413-419 (2003).
18. Zhang, Y. G., et al. Features of intervertebral disc degeneration in rat's aging process. *Journal of Zhejiang University. Science. B* 10, 522-527 (2009).
19. Roberts, S., et al. Matrix metalloproteinases and aggrecanase: their role in disorders of the human intervertebral disc. *Spine* 25, 3005-3013 (2000).
20. Le Maitre, C. L., Freemont, A. J. & Hoyland, J. A. Localization of degradative enzymes and their inhibitors in the degenerate human intervertebral disc. *The Journal of pathology* 204, 47-54 (2004).
21. Bastow, E. R., et al. Hyaluronan synthesis and degradation in cartilage and bone. *Cellular and molecular life sciences: CMLS* 65, 395-413 (2008).
22. Milz, S., et al. Molecular composition and pathology of entheses on the medial and lateral epicondyles of the humerus: a structural basis for epicondylitis. *Annals of the rheumatic diseases* 63, 1015-1021 (2004).
23. Resnick, D., Feingold, M. L., Curd, J., Niwayama, G. & Goergen, T. G. Calcaneal abnormalities in articular disorders. Rheumatoid arthritis, ankylosing spondylitis, psoriatic arthritis, and Reiter syndrome. *Radiology* 125, 355-366 (1977).
24. Bassiouni, M. Incidence of calcaneal spurs in osteoarthrosis and rheumatoid arthritis, and in control patients. *Annals of the rheumatic diseases* 24, 490-493 (1965).
25. Rubin, G. & Witten, M. Plantar calcaneal spurs. *The American journal of orthopedics* 5, 38-41 (1963).
26. Tang, Y., et al. TGF-beta1-induced migration of bone mesenchymal stem cells couples bone resorption with formation. *Nature medicine* 15, 757-765 (2009).
27. Gao, P., et al. Functional effects of TGF-beta1 on mesenchymal stem cell mobilization in cockroach allergen-induced asthma. *Journal of immunology* 192, 4560-4570 (2014).
28. Yang, X., et al. TGF-beta/Smad3 signals repress chondrocyte hypertrophic differentiation and are required for maintaining articular cartilage. *The Journal of cell biology* 153, 35-46 (2001).
29. Shinojima, N., et al. TGF-beta mediates homing of bone marrow-derived human mesenchymal stem cells to glioma stem cells. *Cancer research* 73, 2333-2344 (2013).
30. Grafe, I., et al. Excessive transforming growth factor-beta signaling is a common mechanism in osteogenesis imperfecta. *Nature medicine* 20, 670-675 (2014).
31. Zhen, G., et al. Inhibition of TGF-beta signaling in mesenchymal stem cells of subchondral bone attenuates osteoarthritis. *Nature medicine* 19, 704-712 (2013).
32. Braun, J., et al. Use of immunohistologic and in situ hybridization techniques in the examination of sacroiliac joint biopsy specimens from patients with ankylosing spondylitis. *Arthritis and rheumatism* 38, 499-505 (1995).

33. Claudepierre, P., et al. A relationship between TGF-beta 1 or IL-6 plasma levels and clinical features of spondyloarthropathies. *British journal of rheumatology* 36, 400-401 (1997).
34. Hahn, M., Vogel, M., Pompesius-Kempa, M. & Delling, G. Trabecular bone pattern factor—a new parameter for simple quantification of bone microarchitecture. *Bone* 13, 327-330 (1992).
35. Sarahrudi, K., et al. Elevated transforming growth factor-beta 1 (TGF-beta1) levels in human fracture healing. *Injury* 42, 833-837 (2011).
36. Quinlan, J. F., et al. Transforming growth factor-beta (TGF-beta) in acute injuries of the spinal cord. *The Journal of bone and joint surgery. British volume* 88, 406-410 (2006).
37. Morganti-Kossmann, M. C., et al. TGF-beta is elevated in the CSF of patients with severe traumatic brain injuries and parallels blood-brain barrier function. *Journal of neurotrauma* 16, 617-628 (1999).
38. Varedi, M., Jeschke, M. G., Englander, E. W., Herndon, D. N. & Barrow, R. E. Serum TGF-beta in thermally injured rats. *Shock* 16, 380-382 (2001).
39. Castagnola, P., Moro, G., Descalzi-Cancedda, F. & Cancedda, R. Type X collagen synthesis during in vitro development of chick embryo tibial chondrocytes. *The Journal of cell biology* 102, 2310-2317 (1986).
40. Chen, Q. A., et al. Long-range movement and fibril association of type X collagen within embryonic cartilage matrix. *Proceedings of the National Academy of Sciences of the United States of America* 87, 8046-8050 (1990).
41. Shi, M., et al. Latent TGF-beta structure and activation. *Nature* 474, 343-349 (2011).
42. Mendez-Ferrer, S., et al. Mesenchymal and haematopoietic stem cells form a unique bone marrow niche. *Nature* 466, 829-834 (2010).
43. Ono, N., et al. Vasculature-associated cells expressing nestin in developing bones encompass early cells in the osteoblast and endothelial lineage. *Developmental cell* 29, 330-339 (2014).
44. Itkin, T., et al. Distinct bone marrow blood vessels differentially regulate haematopoiesis. *Nature* 532, 323-328 (2016).
45. Maffulli, N. Rupture of the Achilles tendon. *The Journal of bone and joint surgery. American volume* 81, 1019-1036 (1999).
46. Pennisi, E. Tending tender tendons. *Science* 295, 1011 (2002).
47. Audenaert, E., Van Nuffel, J., Schepens, A., Verhelst, M. & Verdonk, R. Reconstruction of massive rotator cuff lesions with a synthetic interposition graft: a prospective study of 41 patients. *Knee surgery, sports traumatology, arthroscopy: official journal of the ESSKA* 14, 360-364 (2006).
48. Sclamberg, S. G., Tibone, J. E., Itamura, J. M. & Kasraeian, S. Six-month magnetic resonance imaging follow-up of large and massive rotator cuff repairs reinforced with porcine small intestinal submucosa. *Journal of shoulder and elbow surgery/American Shoulder and Elbow Surgeons . . . [et al.]* 13, 538-541 (2004).
49. Jarvinen, T. A., et al. Achilles tendon injuries. *Current opinion in rheumatology* 13, 150-155 (2001).
50. Astrom, M. & Rausing, A. Chronic Achilles tendinopathy. A survey of surgical and histopathologic findings. *Clinical orthopaedics and related research*, 151-164 (1995).
51. Myerson, M. S. & McGarvey, W. Disorders of the Achilles tendon insertion and Achilles tendinitis. *Instructional course lectures* 48, 211-218 (1999).
52. Blaney Davidson, E. N., van der Kraan, P. M. & van den Berg, W. B. TGF-beta and osteoarthritis. *Osteoarthritis and cartilage/OARS, Osteoarthritis Research Society* 15, 597-604 (2007).
53. Zhang, M., et al. Smad3 prevents beta-catenin degradation and facilitates beta-catenin nuclear translocation in chondrocytes. *The Journal of biological chemistry* 285, 8703-8710 (2010).
54. Li, T. F., et al. Smad3-deficient chondrocytes have enhanced BMP signaling and accelerated differentiation. *Journal of bone and mineral research: the official journal of the American Society for Bone and Mineral Research* 21, 4-16 (2006).
55. Vogel, K. G. & Koob, T. J. Structural specialization in tendons under compression. *International review of cytology* 115, 267-293 (1989).
56. Robbins, J. R., Evanko, S. P. & Vogel, K. G. Mechanical loading and TGF-beta regulate proteoglycan synthesis in tendon. *Archives of biochemistry and biophysics* 342, 203-211 (1997).
57. Maeda, T., et al. Conversion of mechanical force into TGF-beta-mediated biochemical signals. *Current biology: CB* 21, 933-941 (2011).
58. Chen, R., et al. Attenuation of the progression of articular cartilage degeneration by inhibition of TGF-beta1 signaling in a mouse model of osteoarthritis. *The American journal of pathology* 185, 2875-2885 (2015).
59. Waning, D. L., et al. Excess TGF-beta mediates muscle weakness associated with bone metastases in mice. *Nature medicine* 21, 1262-1271 (2015).
60. Kim, H. M., et al. The role of transforming growth factor beta isoforms in tendon-to-bone healing. *Connective tissue research* 52, 87-98 (2011).
61. Doschak, M. R., et al. Bisphosphonates reduce bone mineral loss at ligament entheses after joint injury. *Osteoarthritis and cartilage/OARS, Osteoarthritis Research Society* 13, 790-797 (2005).
62. Roberts, A. B., et al. Transforming growth factor type beta: rapid induction of fibrosis and angiogenesis in vivo and stimulation of collagen formation in vitro. *Proceedings of the National Academy of Sciences of the United States of America* 83, 4167-4171 (1986).
63. Nall, A. V., et al. Transforming growth factor beta 1 improves wound healing and random flap survival in normal and irradiated rats. *Archives of otolaryngology—head & neck surgery* 122, 171-177 (1996).
64. Piera-Velazquez, S., Li, Z. & Jimenez, S. A. Role of endothelial-mesenchymal transition (EndoMT) in the pathogenesis of fibrotic disorders. *The American journal of pathology* 179, 1074-1080 (2011).
65. Xu, J., Lamouille, S. & Derynck, R. TGF-beta-induced epithelial to mesenchymal transition. *Cell research* 19, 156-172 (2009).
66. Matt, P., et al. Recent advances in understanding Marfan syndrome: should we now treat surgical patients with losartan? *The Journal of thoracic and cardiovascular surgery* 135, 389-394 (2008).
67. MacCarrick, G., et al. Loeys-Dietz syndrome: a primer for diagnosis and management. *Genetics in medicine: official journal of the American College of Medical Genetics* 16, 576-587 (2014).
68. Ayyavoo, A., Derraik, J. G., Cutfield, W. S. & Hofman, P. L. Elimination of pain and improvement of exercise capacity in Camurati-Engelmann disease with losartan. *The Journal of clinical endocrinology and metabolism* 99, 3978-3982 (2014).
69. Morris, J. C., et al. Phase I study of GC1008 (fresolimumab): a human anti-transforming growth factor-beta (TGFbeta) monoclonal antibody in patients with advanced malignant melanoma or renal cell carcinoma. *PloS one* 9, e90353 (2014).
70. Trachtman, H., et al. A phase 1, single-dose study of fresolimumab, an anti-TGF-beta antibody, in treatment-resistant primary focal segmental glomerulosclerosis. *Kidney international* 79, 1236-1243 (2011).
71. Lacouture, M. E., et al. Cutaneous keratoacanthomas/squamous cell carcinomas associated with neutralization of transforming growth factor beta by the monoclonal antibody fresolimumab (GC1008). *Cancer immunology, immunotherapy: CII* 64, 437-446 (2015).
72. Rice, L. M., et al. Fresolimumab treatment decreases biomarkers and improves clinical symptoms in systemic sclerosis patients. *The Journal of clinical investigation* 125, 2795-2807 (2015).
73. Herbertz, S., et al. Clinical development of galunisertib (LY2157299 monohydrate), a small molecule inhibitor of transforming growth factor-beta signaling pathway. *Drug design, development and therapy* 9, 4479-4499 (2015).
74. Pastar, I., et al. Attenuation of the transforming growth factor beta-signaling pathway in chronic venous ulcers. *Molecular medicine* 16, 92-101 (2010).
75. Kim, B. C., et al. Fibroblasts from chronic wounds show altered TGF-beta-signaling and decreased TGF-beta Type II receptor expression. *Journal of cellular physiology* 195, 331-336 (2003).
76. Nyyssonen, T., Luthje, P. & Kroger, H. The increasing incidence and difference in sex distribution of Achilles tendon rupture in Finland in 1987-1999. *Scandinavian journal of surgery: SJS: official organ for the Finnish Surgical Society and the Scandinavian Surgical Society* 97, 272-275 (2008).
77. McClure, J. The effect of diphosphonates on heterotopic ossification in regenerating Achilles tendon of the mouse. *The Journal of pathology* 139, 419-430 (1983).
78. Chytil, A., Magnuson, M. A., Wright, C. V. & Moses, H. L. Conditional inactivation of the TGF-beta type II receptor using Cre:Lox. *Genesis* 32, 73-75 (2002).

What is claimed is:

1. A method for the treatment of enthesophytes in the Posterior Calcaneal Tuberosity (PCT) and/or enthesis degeneration of the Achilles tendon of a subject in need thereof comprising administering to the subject an effective amount of a transforming growth factor-β (TGF-β) inhibitor.

2. The method of claim 1, wherein the transforming growth factor-β (TGF-β) inhibitor is an antibody which binds TGF-β with high affinity.

3. The method of claim 2, wherein the antibody is selected from the group consisting of 1D11, fresolimumab, and galunisertib.

4. The method of claim 3, wherein the antibody is 1D11.

5. The method of claim 1, wherein the transforming growth factor-β (TGF-β) inhibitor is a biologically active agent which inhibits expression of TGF-β in the cells of the subject.

6. The method of claim 1, wherein the transforming growth factor-β (TGF-β) inhibitor is a biologically active agent which is an antagonist to the TGF-β receptor.

7. The method of claim 1, wherein the TGF-β inhibitor is administered with a pharmaceutically acceptable carrier.

8. The method of claim 1, wherein the TGF-β inhibitor is administered systemically.

9. The method of claim 1, wherein the TGF-β inhibitor is administered locally at the site of an injury or enthesis of the subject.

10. The method of claim 1, wherein the TGF-β inhibitor is administered at a dose of between 0.1 mg/kg to 100 mg/kg.

11. The method of claim 1, wherein the TGF-β inhibitor is administered with at least one additional biologically active agent.

12. The method of claim 11, wherein the at least one biologically active agent is in the class of angiotensin II type 1 receptor ($AT_1$) antagonists.

13. The method of claim 12, wherein the $AT_1$ antagonist is losartan.

* * * * *